(12) United States Patent
Thome et al.

(10) Patent No.: US 10,705,071 B2
(45) Date of Patent: Jul. 7, 2020

(54) MEDICAL INSTRUMENT WITH SHUTTER FOR SEALING A TEST STRIP PORT

(71) Applicant: Roche Diagnostics Operations, Inc., Indianapolis, IN (US)

(72) Inventors: Klaus Thome, St. Leon-Rot (DE); Reiner Stein, Bad Kreuznach (DE); Lars Fischheiter, Ludwigsburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 421 days.

(21) Appl. No.: 15/844,794

(22) Filed: Dec. 18, 2017

(65) Prior Publication Data

US 2018/0120289 A1    May 3, 2018

Related U.S. Application Data

(63) Continuation of application No. PCT/EP2016/065433, filed on Jun. 30, 2016.

(30) Foreign Application Priority Data

Jun. 30, 2015 (EP) ..................................... 15174542

(51) Int. Cl.
*G01N 33/487* (2006.01)
*A61B 5/145* (2006.01)
*G01N 35/00* (2006.01)

(52) U.S. Cl.
CPC ... *G01N 33/48785* (2013.01); *A61B 5/14532* (2013.01); *G01N 33/4875* (2013.01);
(Continued)

(58) Field of Classification Search
CPC ......... G01N 33/48785; G01N 33/4875; G01N 35/00029; A61B 5/14532; A61B 2562/0295; A61B 2562/247
See application file for complete search history.

(56) References Cited

U.S. PATENT DOCUMENTS 8,158,081 B2    4/2012  Scott et al.
2012/0150448 A1  6/2012  Hurd et al.
(Continued)

FOREIGN PATENT DOCUMENTS

WO    2007/010087 A2    1/2007
WO    2011/136306 A1   11/2011

OTHER PUBLICATIONS

International Preliminary Report on Patentability dated Jan. 2, 2018, in Application PCT/EP2016/065433, 7 pages.
(Continued)

*Primary Examiner* — Dennis White
(74) *Attorney, Agent, or Firm* — Roche Diagnostics Operations, Inc.

(57) ABSTRACT

A medical instrument/analyzer for measuring a biological sample using a test strip. The instrument comprises: a housing with an exterior surface, an internal surface, and an interior volume; an analytical unit within the interior volume with a test strip mount; a test strip port between the exterior and the interior surfaces; a shutter configured for sealing the test strip port when closed, wherein the shutter comprises a test strip support aligned with the test strip port and mount when the shutter is in the open position, wherein the shutter has a first sealing surface, the test strip port has a second sealing surface, and the first sealing and second sealing surfaces are configured to mate in the closed position, wherein the shutter comprises a mechanism for moving between the open and the closed position; and an actuator configured for moving the shutter between the open and closed position.

16 Claims, 19 Drawing Sheets

(52) U.S. Cl.
CPC . *A61B 2562/0295* (2013.01); *A61B 2562/247* (2013.01); *G01N 35/00029* (2013.01)

(56) References Cited

U.S. PATENT DOCUMENTS

2014/0123735 A1* 5/2014 Uenosono .............. G01N 33/49
73/61.41
2015/0176053 A1 6/2015 Elder et al.

OTHER PUBLICATIONS

International Search Report dated Sep. 1, 2016, in Application No. PCT/EP2016/065433, 4 pages.
Roche Diagnostics GmbH, ACCU-CHEK® Inform II Blood Glucose Monitoring System Operator's Manual, http://www.accuchekinformii.com/pdf/05234646002_AC12_OpsMan.pdf, Mar. 2013, 124-131, Version 3.0.

* cited by examiner

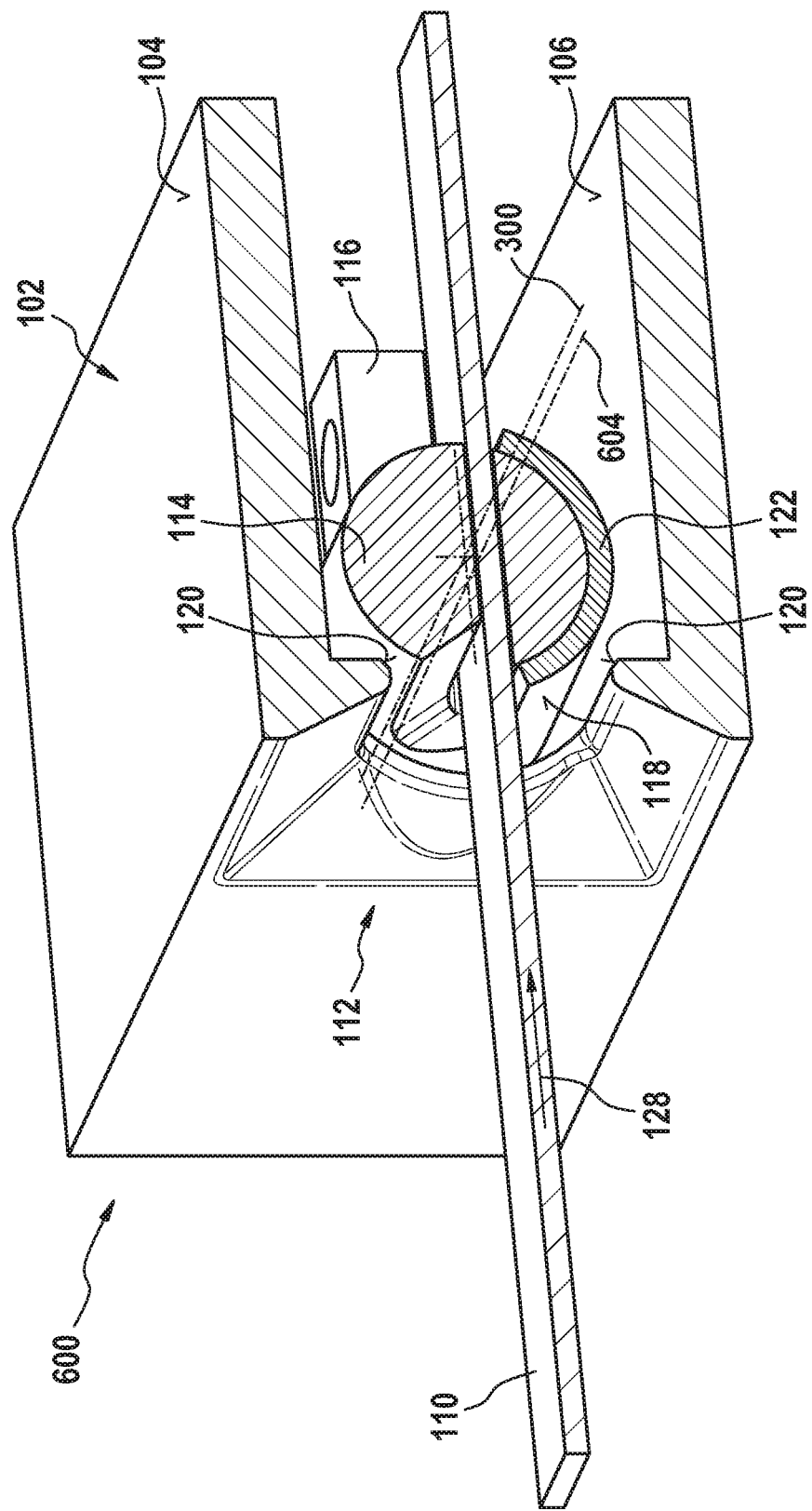

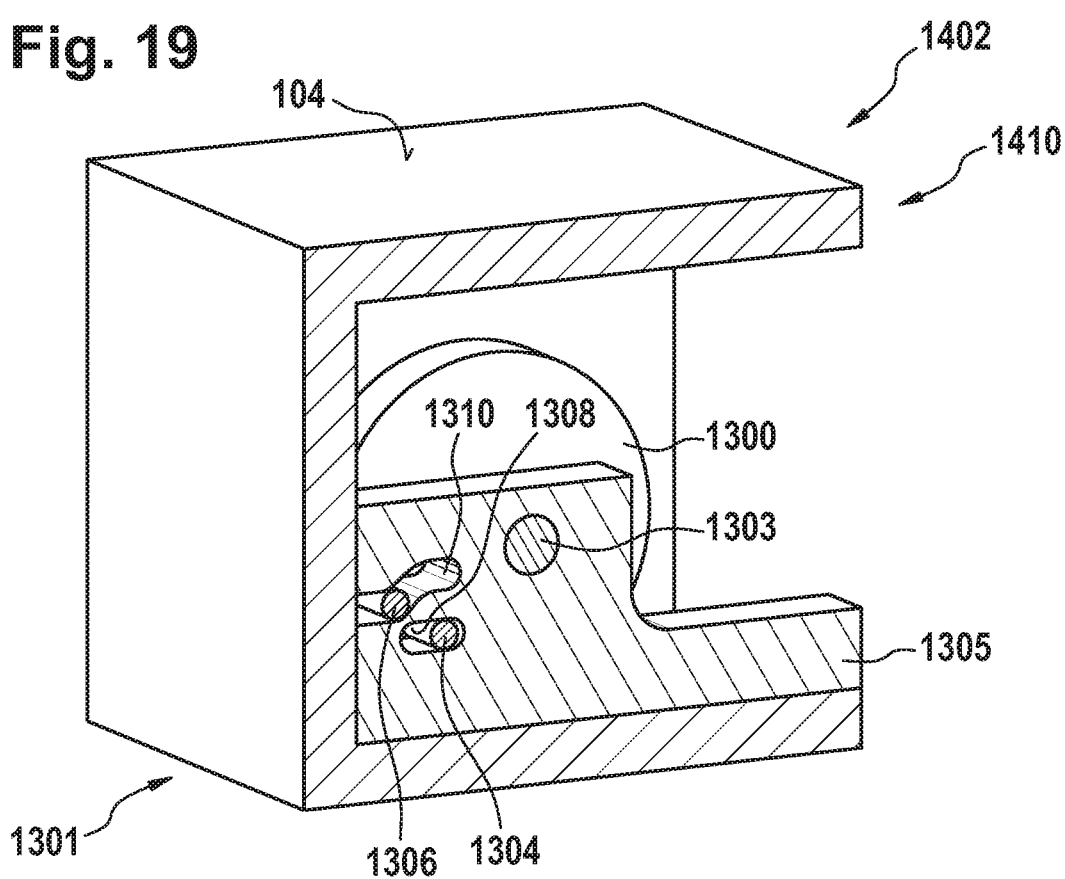
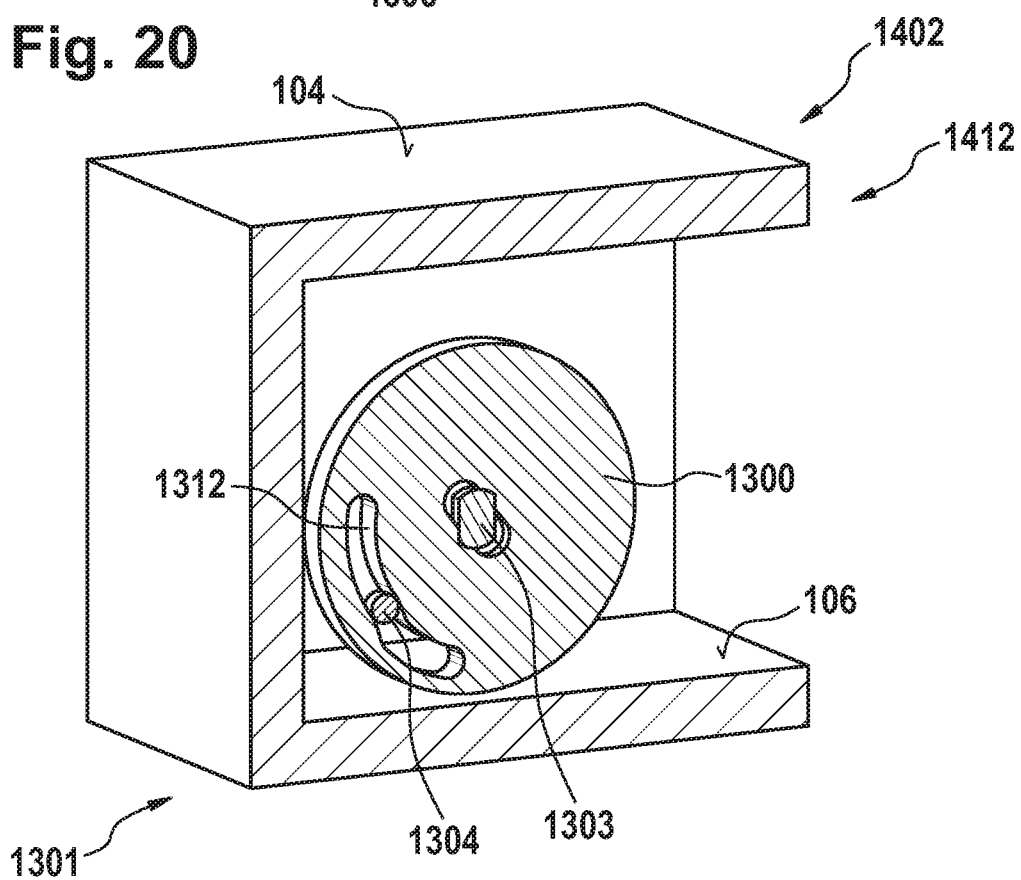

MEDICAL INSTRUMENT WITH SHUTTER FOR SEALING A TEST STRIP PORT

CROSS-REFERENCE TO RELATED APPLICATIONS

This application is a continuation of International Application No. PCT/EP2016/065433, filed 30 Jun. 2016, which claims the benefit of European Patent Application No. 15174542.9, filed 30 Jun. 2015, the disclosures of which are incorporated herein by reference in their entirety.

TECHNICAL FIELD

The present disclosure relates to medical instruments and methods of operating medical instruments and, in particular, to the cleaning and disinfection of test strip ports of analyzers.

BACKGROUND

In hospitals and other clinical settings, healthcare providers may use medical instruments such as test strip readers or analyte monitoring devices to perform diagnostic tests on multiple patients. Current infection control protocols require that the healthcare provider clean the medical instrument between each use or between each patient. This can mean that a particular medical instrument may cleaned thousands of times within the course of a year. It is even possible that a medical instrument may be cleaned tens of thousands of times within its service life.

A typical cleaning and disinfection protocol may require a number of steps. For example the healthcare provider may first clean the medical instrument to remove visible contaminates from its exterior surface. Next the medical device may be disinfected using a disinfecting liquid or a textile impregnated with the disinfecting liquid. After this the medical instrument is allowed to dry.

A challenge in cleaning such medical devices is that fluids used for the cleaning and/or disinfecting steps can destroy electronic components or delicate instruments used for performing the diagnostic tests if such fluids enter into the interior volume of the medical instrument, e.g., via the test element port. Ports used to insert biological samples or test elements or test strips not only need to be sealed against these fluids, but they also need to be able to be reliably sealed for tens of thousands of cycles.

SUMMARY

It is against the above background that the present disclosure provides certain unobvious advantages and advancements over the prior art. In particular, the inventors have recognized a need for improvements in medical instruments with test element port(s) and medical analyzers for performing a measurement on a biological sample using a test strip.

Although the embodiments of the present disclosure are not limited to specific advantages or functionality, it is noted that the present disclosure provides for In accordance with one embodiment of the disclosure, a method of operating a medical instrument is provided, wherein the medical instrument is an analyzer for performing a measurement on a biological sample using a test strip, wherein the medical instrument comprises:

a housing with an exterior surface, wherein the housing comprises an internal surface surrounding an interior volume;

an analytical unit for analyzing the test strip, wherein the analytical unit is within the interior volume, wherein the analytical unit comprises a test strip mount configured for receiving the test strip to perform the measurement;

a test strip port between the exterior surface and the interior surface, wherein the test strip port is configured for receiving the test strip, wherein the test strip port is aligned with the test strip mount along an insertion direction;

a shutter for sealing the test strip port, wherein the shutter is configured for being in an open position and a closed position, wherein the shutter is within the interior volume, wherein the shutter is configured for sealing the test strip port when in the closed position, wherein the shutter comprises a test strip support, wherein the test strip support is aligned with the test strip port and the test strip mount when the shutter is in the open position, wherein the shutter has a first sealing surface, wherein the test strip port has a second sealing surface, wherein the first sealing surface and the second sealing surface are configured to mate in the closed position, wherein the shutter comprises a mechanism for moving the shutter between the open position and the closed position, wherein moving the shutter between the closed position and the open position comprises a rotation of the shutter perpendicular to the insertion direction; and an actuator for actuating the mechanism to move the shutter between the open position and the closed position;

wherein the method comprises the steps of:
  controlling the actuator to actuate the mechanism to move the shutter in the open position;
  placing the biological sample on the test strip;
  inserting the test strip into the test strip port such that the test strip passes through the test strip support and into the test strip mount;
  analyzing the test strip with the analytical unit to perform the measurement;
  removing the test strip from the medical instrument;
  controlling the actuator to actuate the mechanism to move the shutter in the closed position; and
  cleaning the exterior surface of the medical instrument.

In accordance with another embodiment of the disclosure, a medical instrument is provided, wherein the medical instrument is an analyzer for performing a measurement on a biological sample using a test strip, wherein the medical instrument comprises:

a housing with an exterior surface, wherein the housing comprises an internal surface surrounding an interior volume;

an analytical unit for analyzing the test strip, wherein the analytical unit is within the interior volume, wherein the analytical unit comprises a test strip mount configured for receiving the test strip to perform the measurement;

a test strip port between the exterior surface and the interior surface, wherein the test strip port is configured for receiving the test strip, wherein the test strip port is aligned with the test strip mount along an insertion direction;

a shutter for sealing the test strip port, wherein the shutter is configured for being in an open position and a closed position, wherein the shutter is within the interior volume, wherein the shutter is configured for sealing the test strip port when in the closed position, wherein the shutter comprises a test strip support, wherein the test strip support is aligned with the test strip port and the test strip mount when the shutter is in the open position, wherein the shutter has a first sealing surface, wherein the test strip port has a second sealing surface, wherein the first sealing surface and the second sealing surface are configured to mate in the closed position, wherein the shutter comprises a mechanism for moving the shutter between the open position and the closed position, wherein moving the shutter between the closed position and the open position comprises a rotation of the shutter perpendicular to the insertion direction; and an actuator for actuating the mechanism to move the shutter between the open position and the closed position.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present description can be best understood when read in conjunction with the following drawings, where like structure is indicated with like reference numerals and in which:

FIG. 6A shows a perspective view of FIG. 6;

FIG. 19 shows a perspective view of the medical instrument of FIG. 17 at an alternative cross section;

FIG. 20 shows a perspective view of the medical instrument of FIG. 17 at a further alternative cross section;

Figure 1:
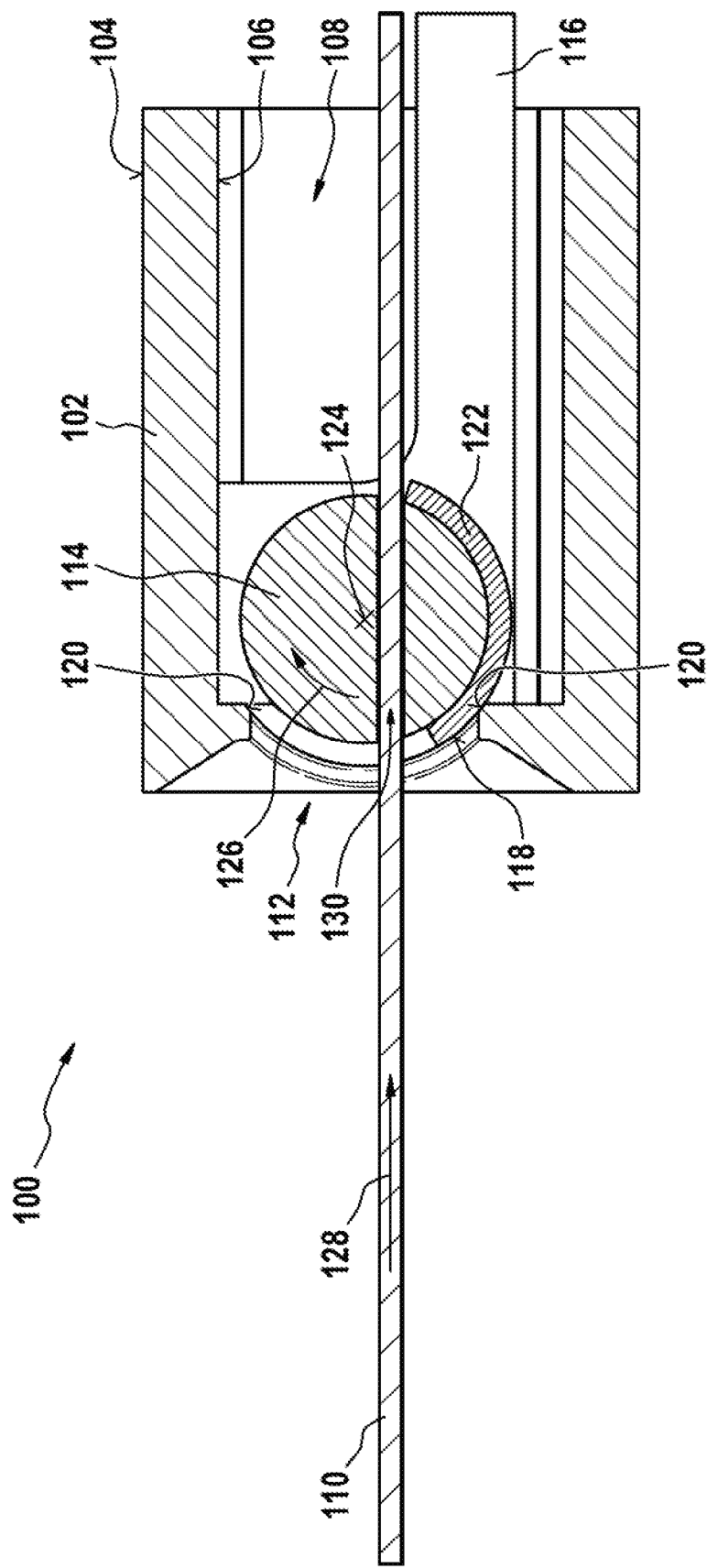
FIG. 1 shows an example of a portion of a medical instrument in accordance with an embodiment of the present disclosure.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

As will be appreciated by one skilled in the art, aspects of the present disclosure may be embodied as an apparatus, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium that may store instructions that are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data that is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory that is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component that is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors.

The computer executable code may be executed by multiple processors, which may be within the same computing device, or which may even be distributed across multiple computing devices.

Computer executable code may comprise machine executable instructions or a program that causes a processor to perform an aspect of the present disclosure. Computer executable code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter that generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described with reference to flowchart illustrations and/or block diagrams of methods, apparatus (systems) and computer program products according to embodiments of the disclosure. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions that execute on the computer or other programmable apparatus provide processes for implementing the functions/acts specified in the flowchart and/or block diagram block or blocks.

In one aspect the present disclosure provides for a method of operating a medical instrument. The medical instrument is an analyzer for performing a measurement on a biological sample using a test strip. The analyzer could for example be a handheld analyzer or a table top analyzer.

A biological sample as used herein encompasses also any chemical product derived, copied, replicated, or reproduced from a sample taken from an organism.

A test strip as used herein encompasses a ribbon-shaped substrate for receiving a liquid biological sample. A test strip is a disposable element containing chemicals that react with the analyte to be determined in the biological sample and is used for a single measurement. The determination of the analyte can be performed using different technologies, e.g., optical and/or electrochemical methods, and therefore the test strip comprises specific measurement structures to perform these measurements, e.g., optical test fields and/or electrode structures.

The medical instrument comprises a housing with an exterior surface. The housing comprises an internal surface surrounding an interior volume. The medical instrument further comprises an analytical unit for analyzing the test strip. The analytical unit is within the interior volume. In other words the analytical unit is inside of the housing of the medical instrument. The analytical unit comprises a test strip mount configured for receiving the test strip to perform the measurement. The test strip can be inserted into the medical instrument such that it mounts in the analytical unit so that the measurement can be made on the biological sample. The medical instrument further comprises a test strip port between the exterior surface and the interior surface. The test strip port is configured for receiving the test strip. The test strip port is aligned with a test strip mount along an insertion direction.

The medical instrument further comprises a shutter for sealing the test strip port. The shutter is configured for being in an open position and a closed position. The shutter is within the interior volume. The shutter is configured for sealing the test strip port when in the closed position. When the shutter is in the open position the test strip can be inserted through the test strip port into the test strip mount. The shutter comprises a test strip support. The test strip support is aligned with the test strip port and the test strip mount when the shutter is in the open position. The shutter has a first sealing surface.

The test strip port has a second sealing surface. The first sealing surface and the second sealing surface are configured to mate in the closed position. By mating that means that the first sealing surface and the second sealing surface seal the test strip port. The shutter comprises a mechanism for moving the shutter between the open position and the closed position. Moving the shutter between the closed position and the open position comprises a rotation of the shutter perpendicular to the insertion direction. There may be additional movements of the shutter when moved between the closed and open position. However, motion of the shutter between the open and closed position comprises a rotation of the shutter perpendicular to the insertion direction.

The medical instrument further comprises an actuator for actuating the mechanism to move the shutter between the open position and the closed position. The actuator for instance may be a motor or other device, which may be controlled by a processor for controlling the medical device for opening and closing the shutter. In other embodiments there may be a mechanism that is actuated by hand. For example a lever or other device might be used for actuating the mechanism.

The method comprises the step of controlling the actuator to actuate the mechanism to move the shutter into the open position. The method starts by the shutter being in the open position. Next, a biological sample is placed onto a test strip. The next step in the method is to insert the test strip into the test strip port such that the test strip passes through the test strip support and into the test strip mount. The steps of placing the sample onto the test strip and inserting the test strip into the test strip port can also be performed in reverse order, in particular if the test strip comprises sample transport structures (e.g., a capillary channel), which can transport the biological sample from a sample application port of the test strip that is located outside of the medical device if the test strip is inserted into the test strip port to the measurement structures of the test strip, which are located inside of the medical device if the test strip is inserted into the test strip port. The test strip is now in a position where the measurement of the biological sample can be performed by the analytical unit. The method further comprises analyzing the test strip with the analytical unit to perform the measurement.

Next, the method comprises removing the test strip from the medical instrument. The next step in the method is to control the actuator to actuate the mechanism to move the shutter into the closed position. The test strip port is now sealed by mating the first sealing surface and the second sealing surface. The method further comprises cleaning the exterior surface of the medical instrument. This embodiment may have the benefit of providing for a medical instrument that can be more readily cleaned. This for instance may be beneficial for test strip analyzers that are used in a clinical situation in a doctor's office or a hospital. In such situations the medical instrument should be cleaned after every use to ensure proper hygiene and reduce the chances that an infection is spread. Having the shutter within the interior volume makes it easier to clean the medical instrument.

In clinical use, healthcare professionals are typically required to follow a cleaning protocol when using a medical instrument more than once. A typical cleaning protocol usually requires the health care professional to clean the outer surface of the medical instrument to ensure that there is no organic material or other containments visible. After this step the medical professional will usually clean the surface with a liquid disinfectant to further clean the surface and kill or deactivate any microorganism such as bacteria or viruses. The liquid disinfectant could, for example, be provided in the form of a wipe or towel that is infused or saturated with the liquid disinfectant. After this cleaning, the health care professional allows the surface to dry and/or wipes it clean. Medical instruments used in clinics or hospitals may be used repeatedly during the day and are cleaned according to such a protocol after each use. This may result the medical instrument being cleaned thousands of times during the lifetime of its usage. The method and medical instrument may provide for a medical instrument that may be more easily cleaned and/or able to better survive repeated cleanings and/or sterilizations.

In another embodiment of the present disclosure the medical instrument is battery powered. The actuator for instance may be powered by the battery. The analytical unit may also be powered by the battery.

In another embodiments, the battery is a rechargeable battery.

In another embodiment the interior volume is hermetically sealed from the exterior surface when the shutter is in the closed position. This may have the benefit that when the shutter is in the closed position the medical instrument may be more readily cleaned.

In another embodiment, the interior volume is watertight when the shutter is in the closed position. It is understood that herein the term "watertight" herein may in some cases apply to either water only, to some liquids, or to liquids in general.

In another embodiment, the interior volume is watertight from the exterior surface when the shutter is in the closed position.

In another embodiment, when the shutter is in the closed position the shutter and test port fit together so tightly that liquid is unable to enter the interior volume through the test port.

It is understood herein that the term "sealed" as used herein means that when the shutter is in the closed position the shutter prevents the transport of gas and/or liquid through the test port.

In another embodiment, the first and second sealing surfaces may have different properties. For example, one could have a flexible surface such as a gasket and one could be a rigid or hard surface. In another example both surfaces may be similar, both may for example have a flexible or gasket-like surface.

In another embodiment the actuator is a manually operated lever, wheel, or crank.

In another embodiment the actuator may be a motor, stepper motor or other actuator, e.g., a stroke magnet.

In another embodiment the test strip is inserted before a sample is placed on the test strip. In another example the sample would be placed on the test strip and then the biological sample may be drawn into the strip via capillary forces. Then after this has happened the test strip would be inserted into the test strip port.

In another embodiment the test strip support is not aligned with the test strip port and the test strip mount when in the closed position. For example it may make it impossible to close the shutter when there is a test strip in the test strip port.

In another aspect the present disclosure provides for a medical instrument. The medical instrument is an analyzer for performing a measurement on a biological sample using a test strip. The medical instrument comprises a housing with an exterior surface. The housing comprises an internal surface surrounding an interior volume. The medical instrument further comprises an analytical unit for analyzing the test strip. The analytical unit is within the interior volume. The analytical unit comprises a test strip mount configured for receiving the test strip to perform the measurement. The medical instrument further comprises a test strip port between the exterior surface and the interior surface. The test strip port is configured for receiving the test strip. The test strip port is aligned with the test strip mount along an insertion direction. The medical instrument further comprises a shutter for sealing the test strip port. The shutter is configured for being in an open position and a closed position.

The shutter is within the interior volume. The shutter is configured for sealing the test strip port when in the closed position. The shutter comprises a test strip support. The test strip support is aligned with the test strip port and the test strip mount when the shutter is in the open position. The shutter has a first sealing surface. The test strip port has a second sealing surface. The first sealing surface and the second sealing surface are configured to mate in the closed position. The shutter comprises a mechanism for moving the shutter between the open position and the closed position. Moving the shutter between the closed position and the open position comprises a rotation of the shutter perpendicular to the insertion direction. The medical instrument further comprises an actuator for actuating the mechanism to move the shutter between the open position and the closed position.

In another embodiment the actuator is a motor. The medical instrument further comprises a memory for storing machine-executable instructions. The medical instrument further comprises a processor for controlling the medical instrument. Execution of the machine-executable instructions causes the processor to control the motor to actuate the mechanism to move the shutter in an open position. Execution of the machine-executable instructions further cause the processor to analyze the test strip with the analytical unit to perform the measurement when the test strip is inserted into the test strip mount and the biological sample is placed on the test strip.

Execution of the machine-executable instructions further cause the processor to control the motor to actuate the mechanism to move the shutter in the closed position when the test strip is removed from the test strip mount and the test strip port. In some examples the medical instrument may automatically detect when the test strip is removed and controls the motor automatically. In other examples there may be a button or other user interface which the operator of the medical instrument uses to inform the processor that the test strip has been removed.

In another embodiment the first sealing surface is cylindrical about a first cylindrical axis. The second sealing surface is cylindrical about a second cylindrical axis. The first cylindrical axis is parallel with the second cylindrical axis.

In another embodiment the first cylindrical axis is the same as the second cylindrical axis.

In another embodiment the first sealing surface has a convex cross-section that is a circular arc with a first radius. The second sealing surface has a concave cross-section that is a second circular arc with a second radius.

In another embodiment the mechanism is a pivot that rotates the shutter about the first cylindrical axis. The first cylindrical axis is coaxial with the second cylindrical axis. In this example the shutter is simply a cylinder that rotates into place to seal the test strip port.

In another embodiment the mechanism is a pivot that rotates the shutter around a rotational axis. The rotational axis is parallel to the first cylindrical axis. The rotational axis is offset from the first cylindrical axis. In some examples the first radius is the same as the second radius. In other examples the first radius is smaller than the second radius. In this example the first cylindrical axis and the second cylindrical axis are offset from each other. This example may have the benefit that the gasket sealing surface of the sealing surfaces is not necessarily always in contact. For example the shutter could be a cylinder or portion of a cylinder that is offset and when it is rotated into place then the first sealing surface and the second sealing surface seal. This may reduce the amount of friction or wear between the first sealing surface and the second sealing surface.

In another embodiment the mechanism is formed by the shutter, a cam disc, and a fixed support. The first cam disc is configured for rotating relative to the fixed support. The fixed support is rigidly connected to the internal surface of the housing. The shutter comprises a first movable pivot and a second movable pivot. The rigid support comprises a first pathway for guiding the first movable pivot. The rigid support comprises a second pathway for guiding the second movable pivot. The first cam disc comprises a third pathway for guiding the first movable pivot.

In another embodiment the mechanism is a linkage. For example the cams of the previous embodiment may be replaced by a linkage.

In another embodiment the mechanism comprises two identical mechanism portions that support the shutter. For example the shutter may be a cylinder type or approximately-shaped structure. There may be in some examples a mechanism on either side of the shutter to support it. In one example there may be two identical or equivalent mechanisms that support the shutter on both sides.

In another embodiment the medical instrument further comprises a user interface for receiving user input that indicates that the medical instrument has been cleaned. Execution of the machine-executable instructions further cause the processor to control the motor to activate the mechanism to move the shutter in the open position after receiving the user input.

In another embodiment the medical instrument further comprises a detector for detecting if a test strip is inserted through the test strip port. Execution of the machine-executable instructions further cause the processor to control the motor to place the shutter in the closed position after the detector indicates that the test strip is no longer inserted through the test strip port. For example, once a test strip is inserted into the test strip port whenever one is removed the shutter automatically closes. In some examples the detector for detecting if the test strip is inserted could be an optical detector. In other examples the detector may be a mechanical switch actuated if a test strip is inserted through the test strip port.

In another embodiment, the test strip support is a hole within the shutter. Having the test strip support as a hole within the shutter may have the advantage that the test strip support is kept clean when the shutter is closed and when the medical instrument is cleaned, cleaning agent would not be able to come into contact with the test strip support.

In another embodiment the test strip support is a hole within the shutter which has any one of the following: a rectangular profile perpendicular to the insertion direction when in the open position, an oval profile perpendicular to the insertion direction when in the open position, and a profile that transitions from an oval profile near the test strip port to a rectangular profile near the test strip mount when in the open position.

In another embodiment the analytical unit is an optical test strip analyzer.

In another embodiment the analytical unit is an electrochemical test strip analyzer.

In another embodiment the analytical unit is a combination of an optical test strip analyzer and an electrochemical test strip analyzer.

It is understood that one or more of the aforementioned embodiments of the disclosure may be combined as long as the combined embodiments are not mutually exclusive.

In order that the embodiments of the disclosure may be more readily understood, reference is made to the following examples, which are intended to illustrate but not limit the scope thereof.

To measure the concentration of analytes in a body fluid, e.g., a glucose concentration from a small droplet of blood, disposable electrochemical capillary sensor test strips in combination with a meter to determine the concentration are used. For receiving the sensor strip there is a hole in the shell of the meter, commonly referred to as "strip-port" or a "test strip port."

In current medical instruments the strip-port is always open and there is no possibility to close it.

Because the strip-port is always open, the inner part of the meter is not prevented from contamination from outside. Fluids, dust and anything else can come through the hole of the strip-port to the interior of the meter. This can cause a technical fault, up to uselessness of the meter.

In the professional use case it is, e.g., required, that the complete meter get cleaned and disinfected after every test or every patient. Therefore also the strip-port has to be cleaned and disinfected. It is likely that a small amount of cleaning or disinfection agents will come through the hole of the strip-port into the interior of the meter. Some of these agents are very aggressive and the risk that the meter gets damaged is high.

Examples may have the feature of closing the strip-port every time it is not used. This means, that the strip-port only is open when a strip is inserted in the meter. When the measurement is ready and the strip is removed, the strip-port directly gets closed. The fastener or shutter is designed in the shape that the interior of the meter is prevented of contamination. Even when the strip-port get cleaned and disinfected, e.g., by whipping above the surface of the strip-port (e.g., with Clorox-wipes), there is no risk of contamination and the meter is prevented from technical faults and damages. Therefore regulatory requirements are fulfilled.

It is beneficial to make sure that the meter can be cleaned and disinfected very well. Therefore the surface of the meter and especially the area of the strip-port have to be as smooth as possible. To ensure that, the complete mechanical system is an inner part of the meter and on the surface of the meter there are no notches or chamfers.

The fastener can be a cylindrical part with a square diametric hole. The cylinder rotates around a centrically axis. The bearing of this axis is assembled to the housing or a chassis, in the way that the axis can rotate in the bearing. In the area of the strip-port, the housing has an opening, so that the cylindrical part forms also a portion of the exterior surface of the meter. The square hole from the cylindrical part can be located in the middle of the opening of the housing. On the surface of the cylindrical part there is a gasket.

When the strip-port is closed, the square hole of the cylindrical part is located inside of the meter and the gasket has contact with the housing. The housing, gasket and cylindrical part form a sealing. Therefore, the inner part is protected from contamination.

To open the strip-port, the cylindrical part rotates in the way that the square hole is located in front of the opening of the housing. Now it is possible to insert the strip through the opening of the housing and the square hole of the cylindrical part.

FIG. 1 shows a portion of a medical instrument 100. This portion shows a part of the housing 102. The housing has an exterior surface 104 and an internal surface 106. Surrounded by the internal surface 106 is an interior volume 108. A test strip 110 is shown that has been inserted into a test strip port 112. There is a shutter 114 within the interior volume 108. The shutter is shown in the open position in FIG. 1. The shutter 114 is mounted onto a support structure 116. The support structure 116 is attached to the internal surface 106. The shutter has a first sealing surface 118. The test strip port 112 has a second sealing surface 120. In this example the first sealing surface is formed by a gasket material 122 that can be compressed against the second sealing surface 120. Both the first sealing surface 118 and the second sealing surface 120 have a same cylindrical profile about an axis indicated by the pivot 124.

The shutter 114 can be rotated about the pivot 124 in the rotation direction 126. The gasket material 122 will then rotate into place and be compressed against the second sealing surfaces 120. This causes the test strip port 112 to become sealed. When in the open position as is shown in FIG. 1 the test strip 110 can be inserted along an insertion direction 128. The shutter 114 has a test strip support 130. In this example it is a hole which becomes aligned with the test strip port 112 and a test strip mount which is not shown in this FIG. 1.

Figure 2:
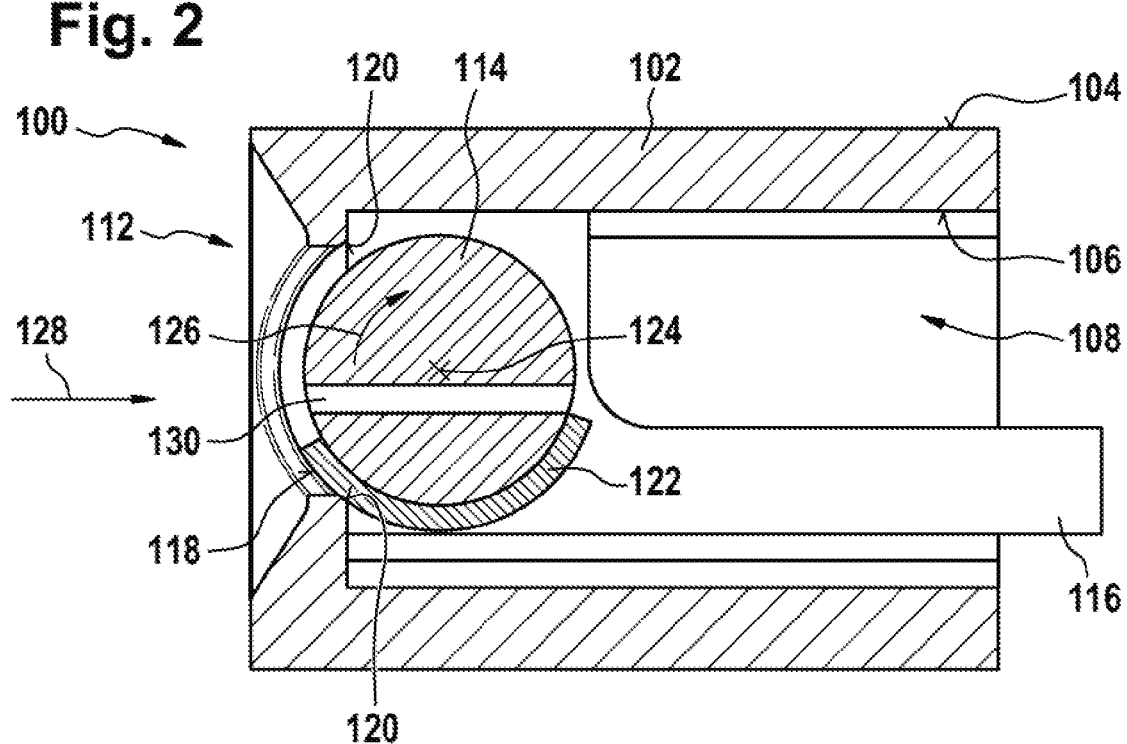
FIG. 2 shows a further view of the medical instrument of FIG. 1 with the shutter in the open position.

FIG. 2 shows a cross-sectional view of the portion of the medical instrument that was shown in FIG. 1. The difference between FIG. 2 and FIG. 1 is that the test strip 110 has not been inserted into the test strip port 112 and the test strip support 130.

Figure 3:
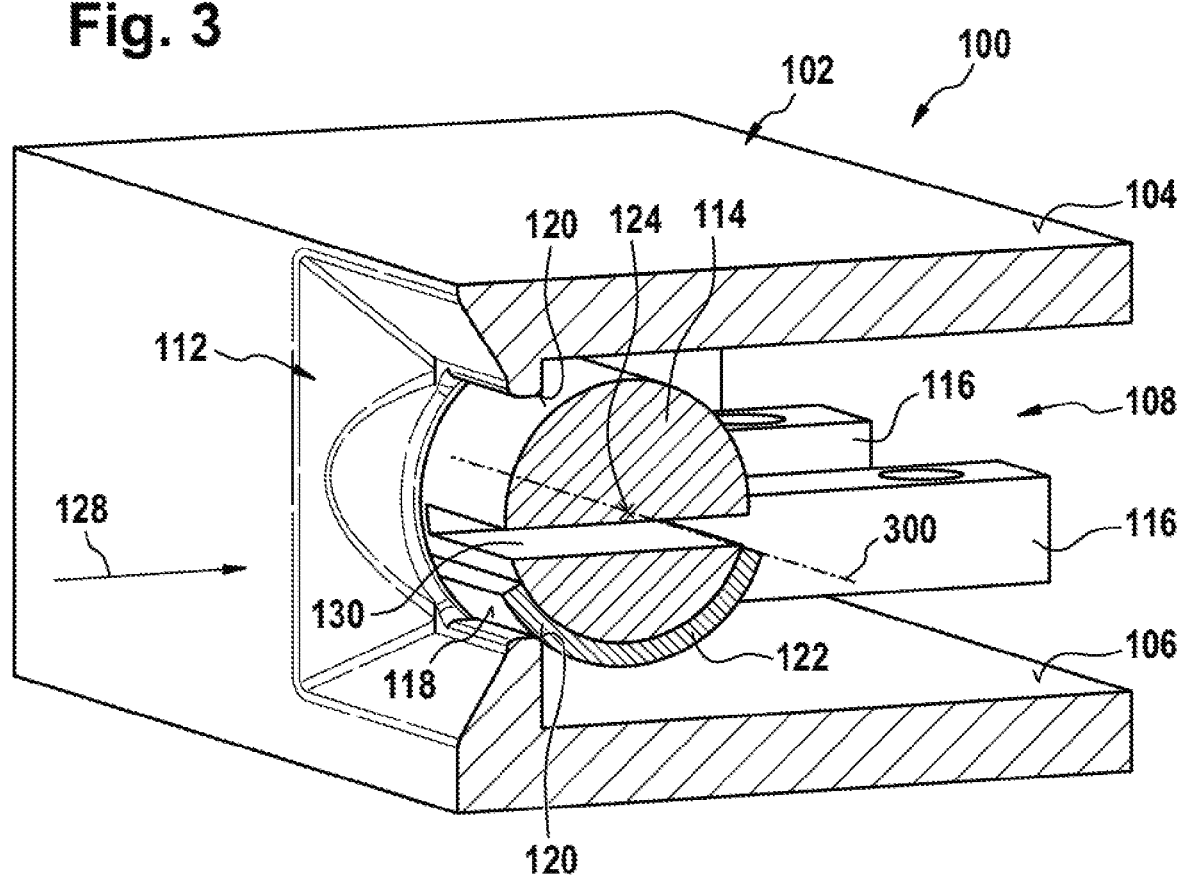
FIG. 3 shows a further view of the medical instrument of FIG. 1 with the shutter in the open position.

FIG. 3 shows a perspective view of the cross-sectional view of FIG. 2. In both FIGS. 2 and 3 the shutter 114 is in the open position. In FIG. 3 a first cylindrical axis 300 can be seen. This first cylindrical axis 300 passes through the pivot 124.

Figure 4:
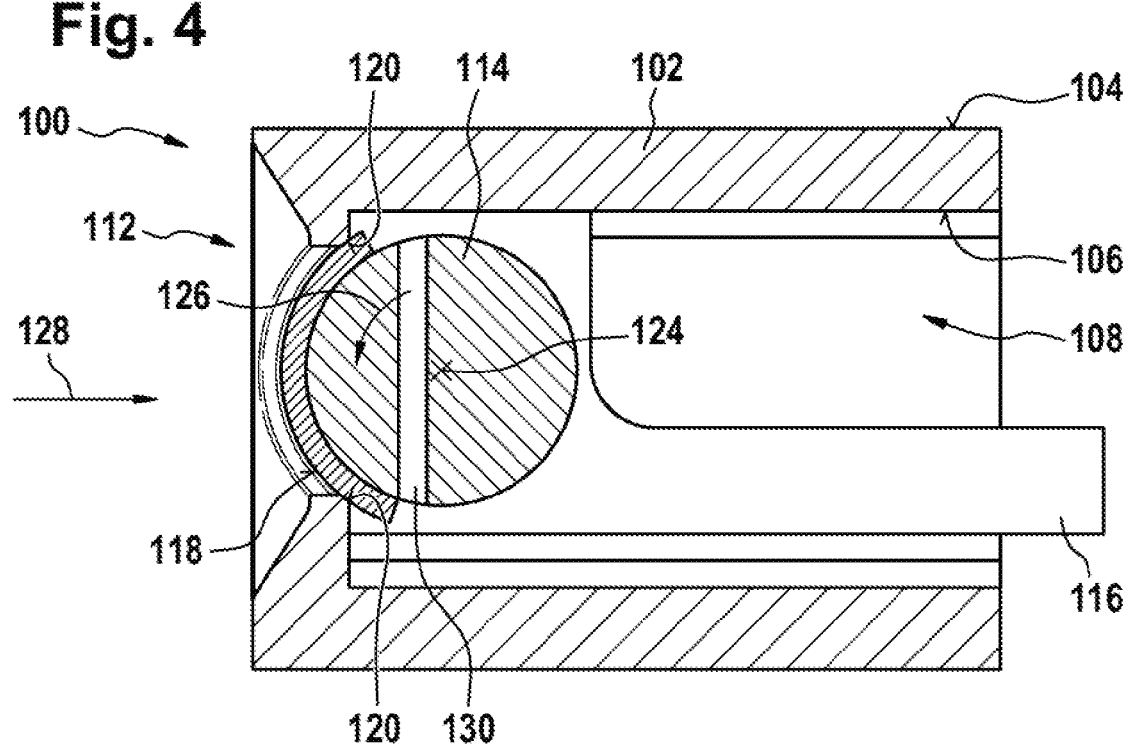
FIG. 4 shows a further view of the medical instrument of FIG. 1 with the shutter in the closed position.
Figure 5:
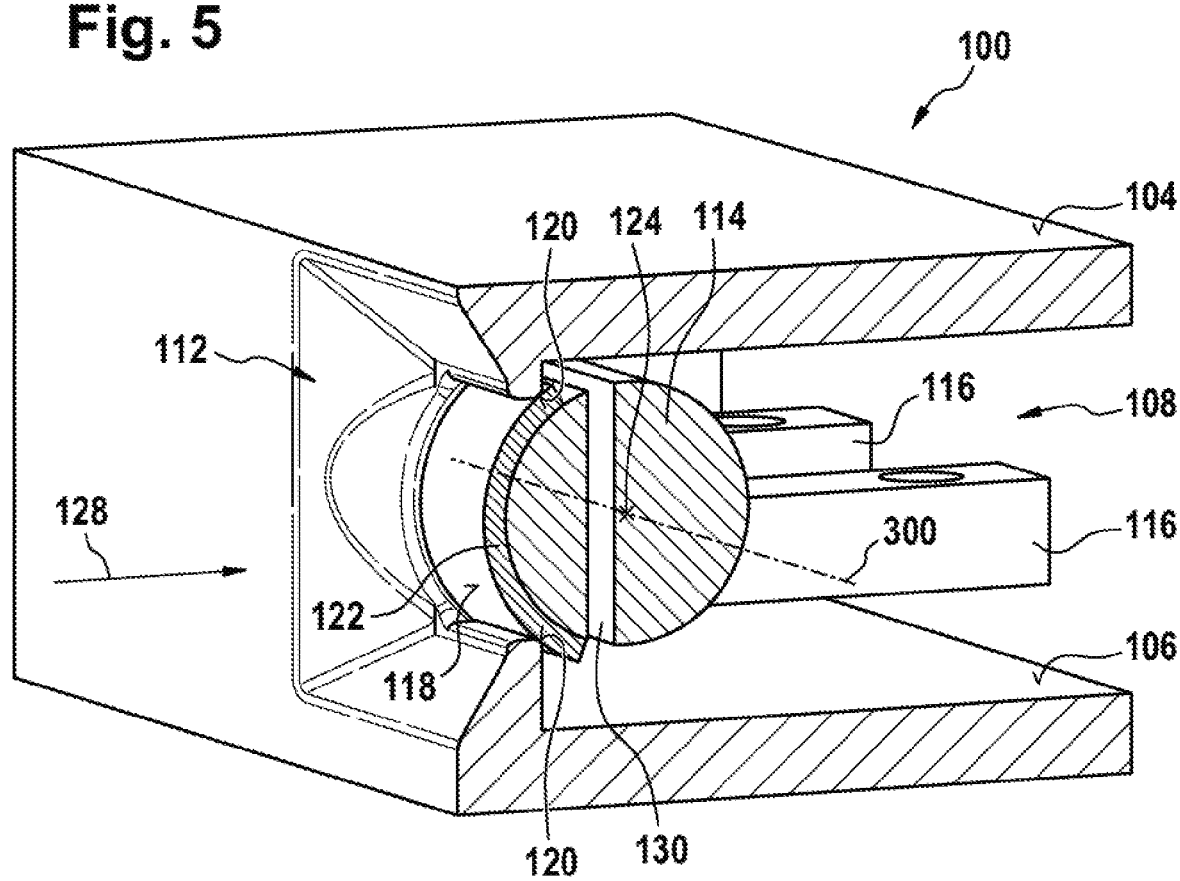
FIG. 5 shows a further view of the medical instrument of FIG. 1 with the shutter in the closed position.

FIG. 4 is similar to FIG. 2 except the shutter 114 has been rotated into the closed position. FIG. 4 shows a cross-sectional view. FIG. 5 shows a perspective view of the cross-sectional view of FIG. 4. It can be seen that both the second sealing surfaces 120 are sealed against the first sealing surface 118. The test strip port 112 is sealed. The test strip support 130 is no longer aligned with the insertion direction 128 or the test strip port 112. It can be seen that the exterior surface 104 is now isolated from the internal surface 106. When the shutter 114 is in the closed position as is shown in FIG. 4 the exterior surface 104 may then be cleaned.

Figure 6:
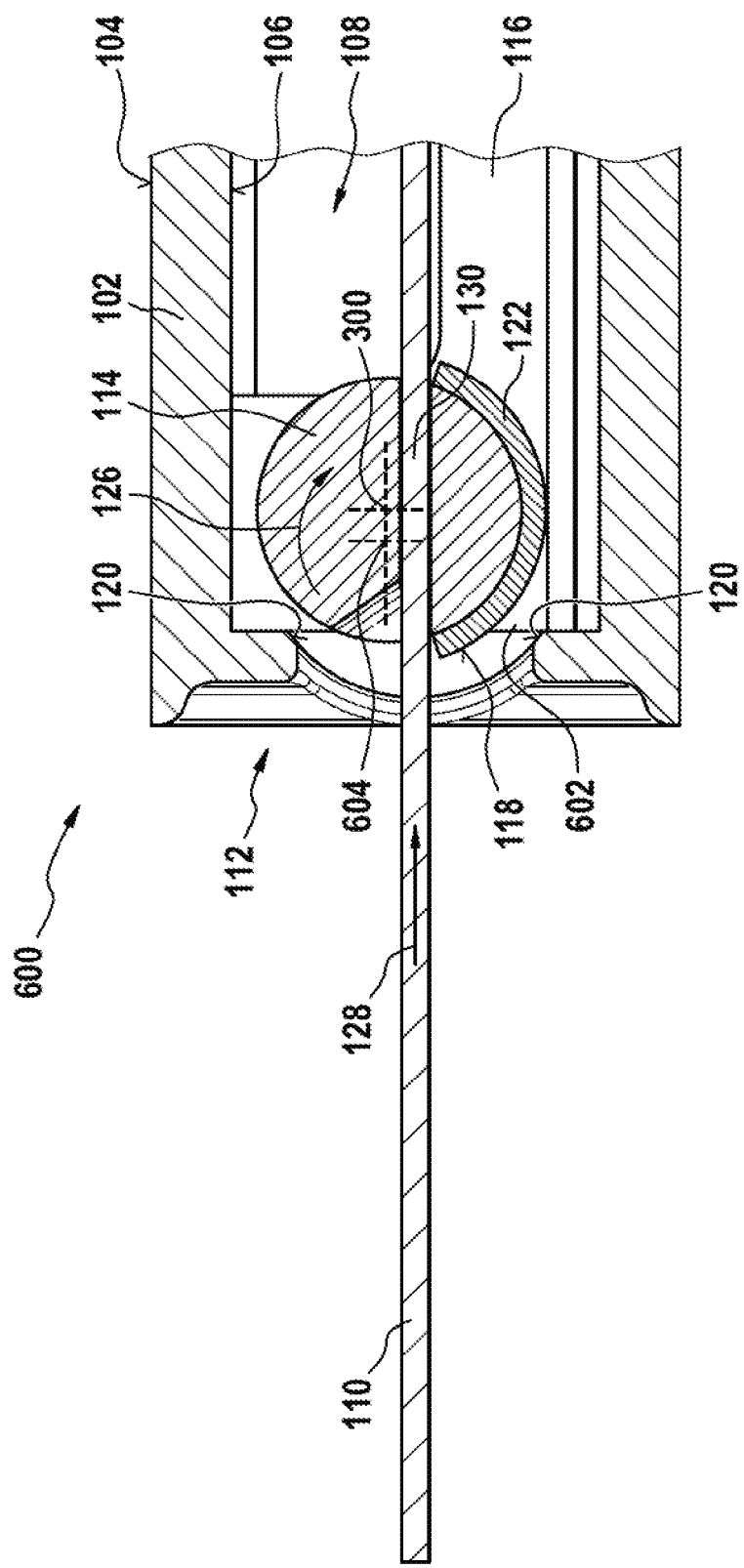
FIG. 6 shows a further example of a portion of a medical instrument in accordance with an embodiment of the present disclosure.

FIG. 6 shows a further example of a portion of the medical instrument 600. The example shown in FIG. 6 is similar to that shown in FIG. 1. A difference is that the pivot in FIG. 6 is not mounted at a symmetry point of the shutter 114. In FIG. 6 there are two dashed crosses marked, 300 and 604. 300 is a first cylindrical axis and is the rotational axis of symmetry for the second sealing surface 120. The shutter, however, does not rotate about the first axis 300—it is mounted such that it rotates about a rotational axis 604. The rotational axis 604 is also an axis of cylindrical symmetry for the first sealing surface 118 and is a second cylindrical axis 604. It can be seen that there is now a gap 602 between the second sealing surface 120 and the first sealing surface 118. As the shutter 114 is rotated in the direction 126 the shutter 114 not only rotates about its pivot, which is coaxial with the rotational axis 604, but also is brought into contact with the second sealing surfaces 120. This may reduce the amount of friction on the first sealing surface 118 when the shutter 114 is closed. Because the shutter 114 rotates about the rotational axis 604, it moves the seal opposite to the direction 128 as it is rotated.

In accordance with another embodiment of the disclosure, the cylindrical part rotates not around a centrically axis, but around an eccentric axis. The system is designed in the way, that only in the closed position of the strip-port the gasket of the cylindrical part has full contact with the housing and the sealing is tight. If the cylindrical part rotates slightly, the eccentrically bearing has the effect that a gap between housing and gasket arise.

The advantage is that there is only a small area where friction between gasket and housing occur.

As a further alternative, the shutter could have a first sealing surface that is elliptically shaped and not symmetrical about the cylindrical axis. This may have an equivalent function as using an eccentric axis with a cylindrically shaped shutter and first sealing surface.

FIG. 6A shows the same view as FIG. 6, except in a perspective view. The position of the first axis 300 and the second axis 604 are shown as dashed lines.

Figure 7:
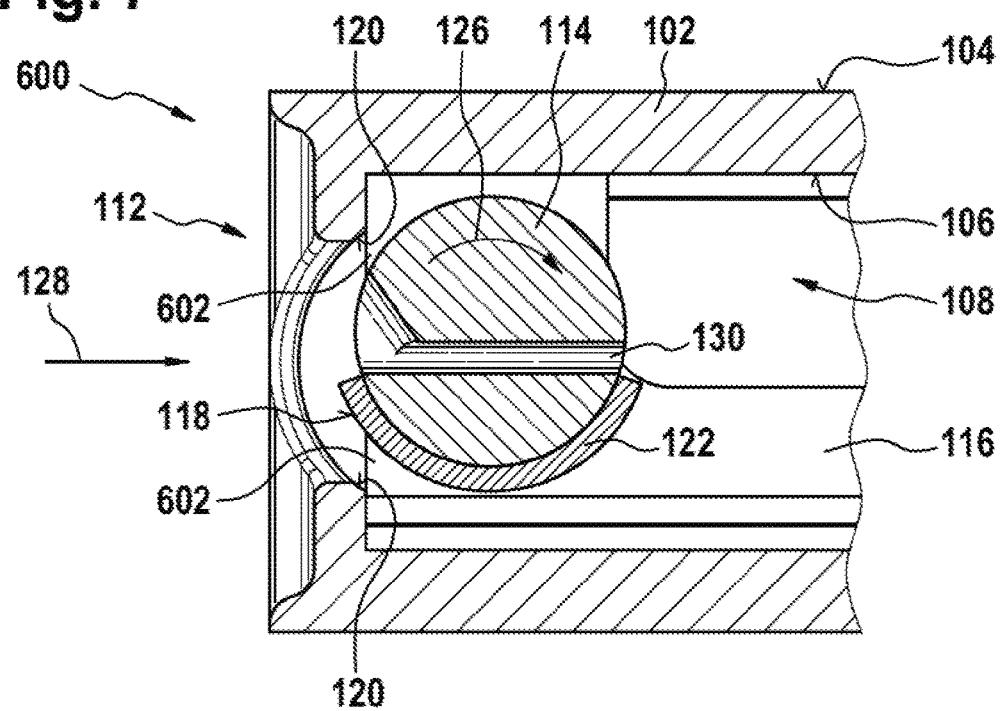
FIG. 7 shows a further view of the medical instrument of FIG. 6 with the shutter in the open position.
Figure 8:
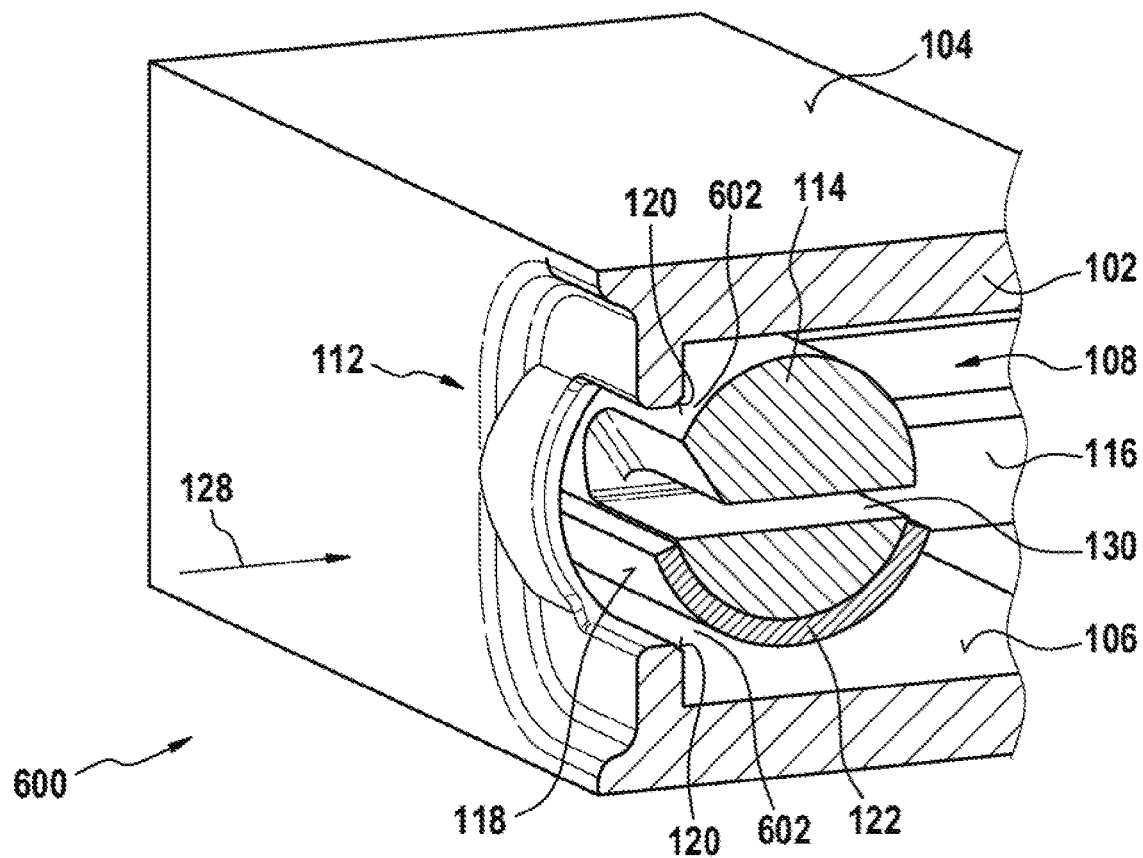
FIG. 8 shows a further view of the medical instrument of FIG. 6 with the shutter in the open position.

FIGS. 7-12 show the shutter of FIG. 6 going from a completely open to a completely closed position. FIGS. 7 and 8 shows the shutter 114 opened. In this position the strip support 130 is aligned with the insertion direction 128. FIG. 7 is a cross-sectional view and FIG. 8 is a perspective of the cross-section of FIG. 7. It can be seen that near the second sealing surfaces 120 there is a large gap 602 between second sealing surface and the first sealing surface 118.

Figure 9:
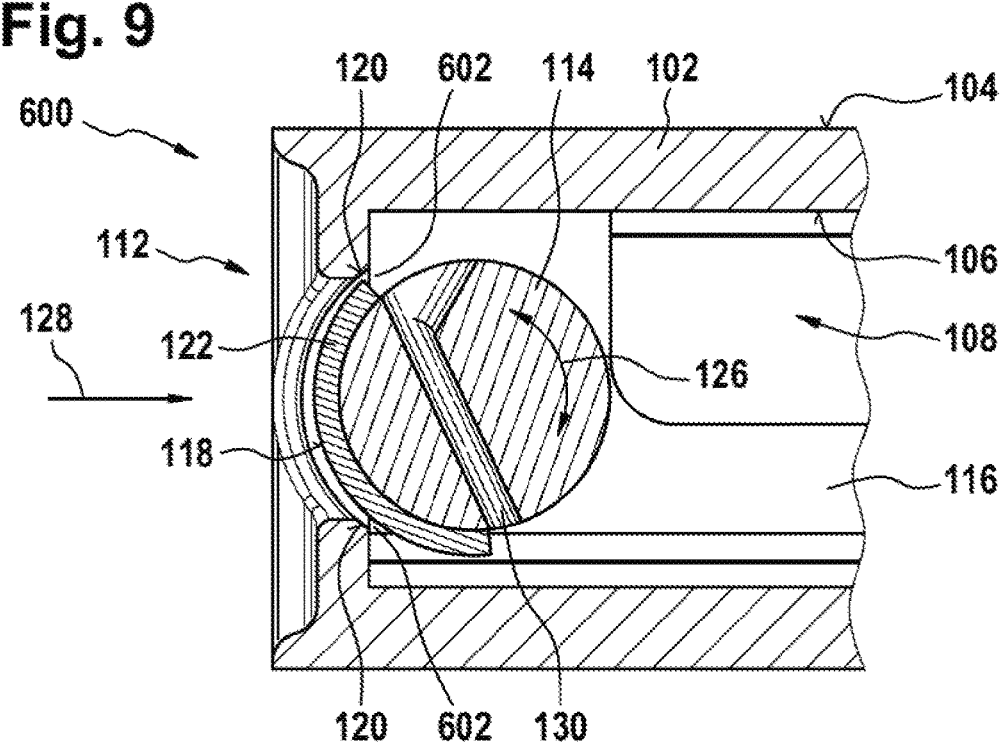
FIG. 9 shows a further view of the medical instrument of FIG. 6 with the shutter in an intermediate position.
Figure 10:
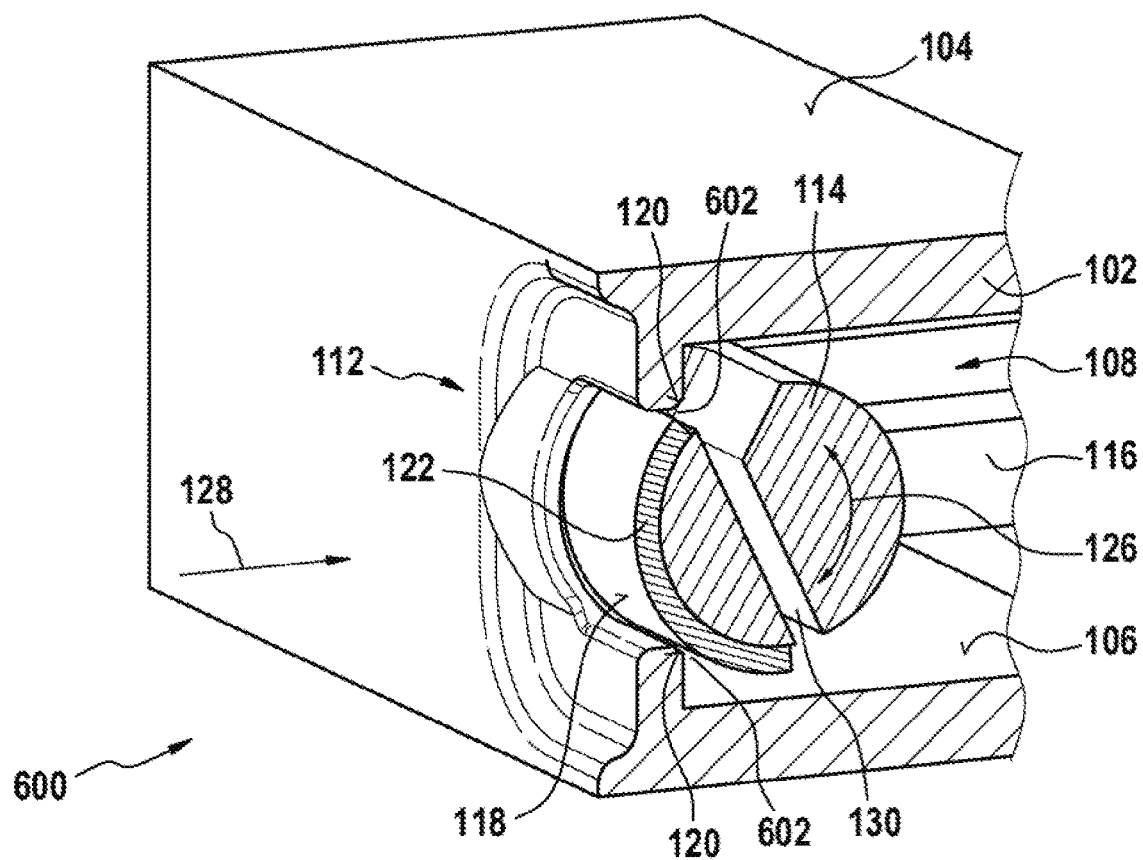
FIG. 10 shows a further view of the medical instrument of FIG. 6 with the shutter in an intermediate position.

FIGS. 9 and 10 show the same shutter 114 in an intermediate position. FIG. 9 is a cross-sectional view and FIG. 10 is a perspective view of the cross-section of FIG. 9. In these Figs. it can be seen that not only has the shutter rotated but that also the gap 602 between the first sealing surface 118 and the second sealing surfaces 120 has reduced. This is because the shutter is mounted off axis and as the shutter 114 rotates it approaches the second sealing surfaces 120. In FIGS. 9 and 10 the test strip support 130 is no longer aligned with the insertion direction 128. However, there is still a gap 602 and the interior volume 108 through the test strip port 112 is not yet sealed.

Figure 11:
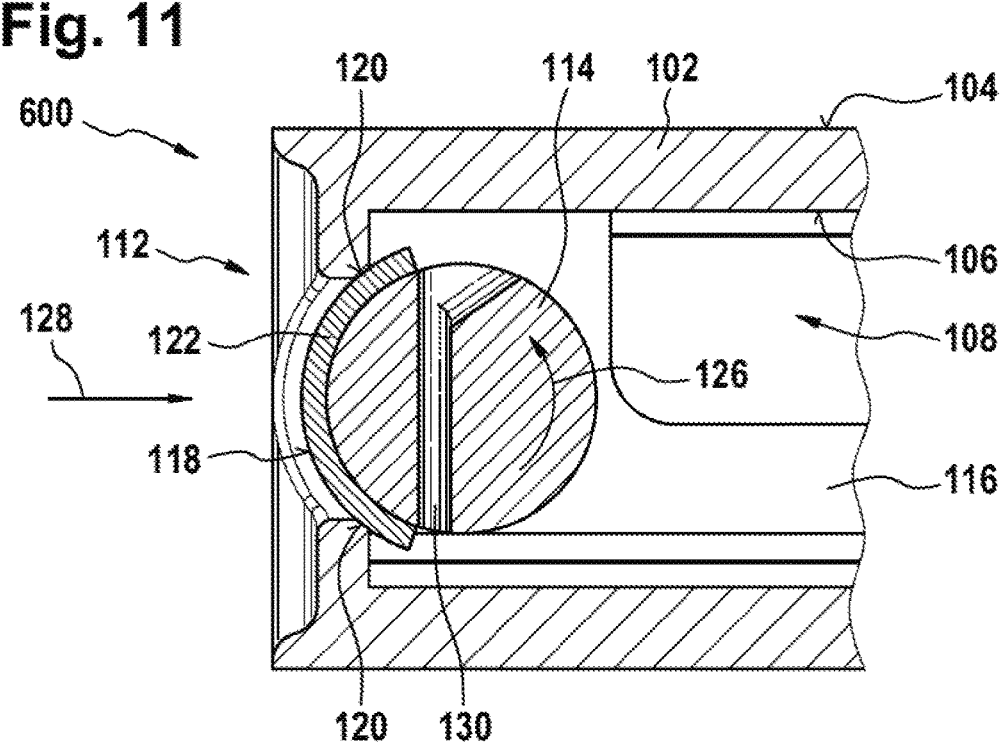
FIG. 11 shows a further view of the medical instrument of FIG. 6 with the shutter in the closed position.
Figure 12:
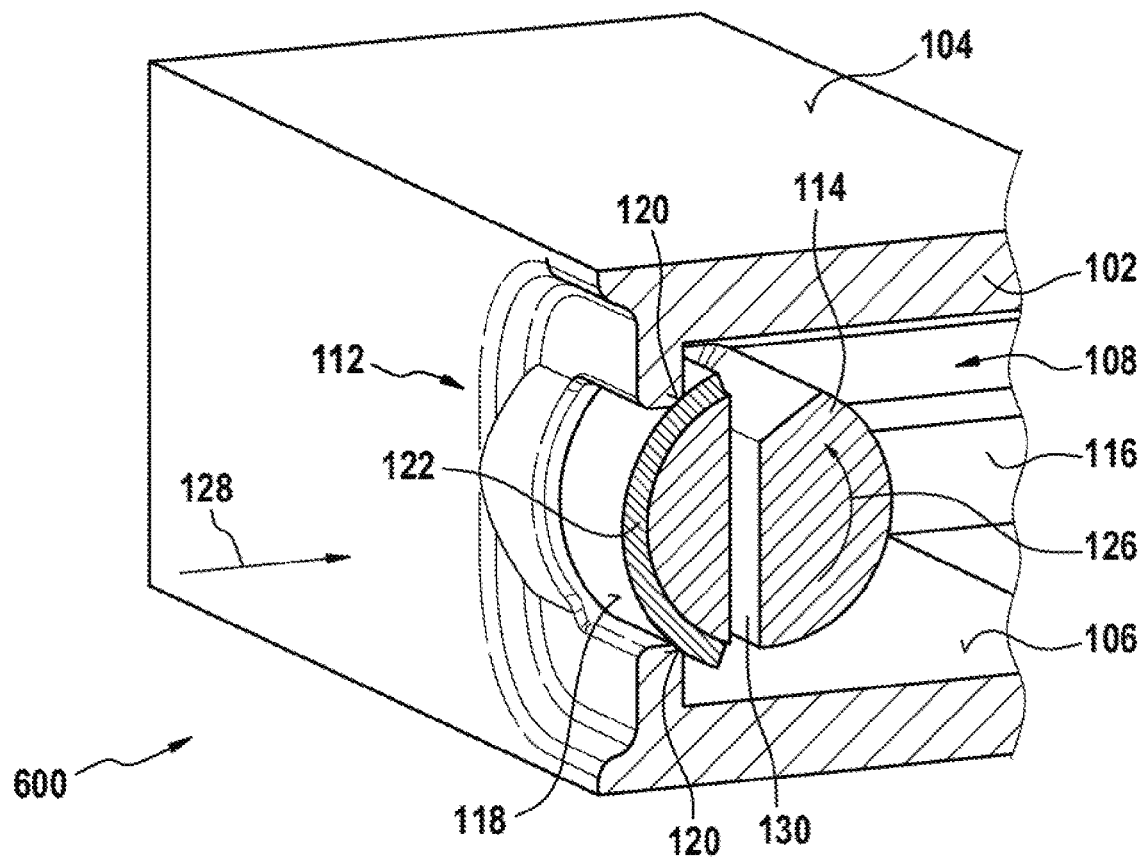
FIG. 12 shows a further view of the medical instrument of FIG. 6 with the shutter in the closed position.

FIGS. 11 and 12 show the shutter 114 in the closed position. FIG. 11 is a cross-sectional view and FIG. 12 is a perspective view of the cross-section of FIG. 11. As can be seen in FIGS. 11 and 12 there is no longer any gap between the second sealing surface 120 and the first sealing surface 118. The insertion direction 128 is blocked by the shutter 114 and the interior volume 108 is now sealed from the exterior exterior surface 104 through the test strip port 112. To open the test strip port 112 the shutter 114 can be rotated in the rotation direction labeled 126.

In accordance with another embodiment of the disclosure, the movement of the cylindrical part is not only a centrically or eccentric movement. The movement can be divided in two sequences: A rotating and a linear sequence. The two sequences are realized with an link motion system. The cylindrical part is mounted in a cam disk. This cam disk is mounted in the housing or a chassis.

The link motion is designed in the way, that there is a gap between gasket and housing in the opened position of the strip-port. When the strip-port gets closed, the cylindrical part at first rotates and then makes the linear movement. With the linear movement the gap between housing and gasket get closed and the sealing is tight. By opening the strip-port, at first the linear movement occurs and then the cylindrical part rotates. An advantage of this embodiment may be that there is no friction, because of the rotation, between gasket and housing anymore.

FIGS. 13-24 illustrate a different example of how the shutter can be constructed. In these Figs. two cam discs are used to rotate and translate the shutter 114. The shutter is shown in three different positions in various views.

Figure 15:
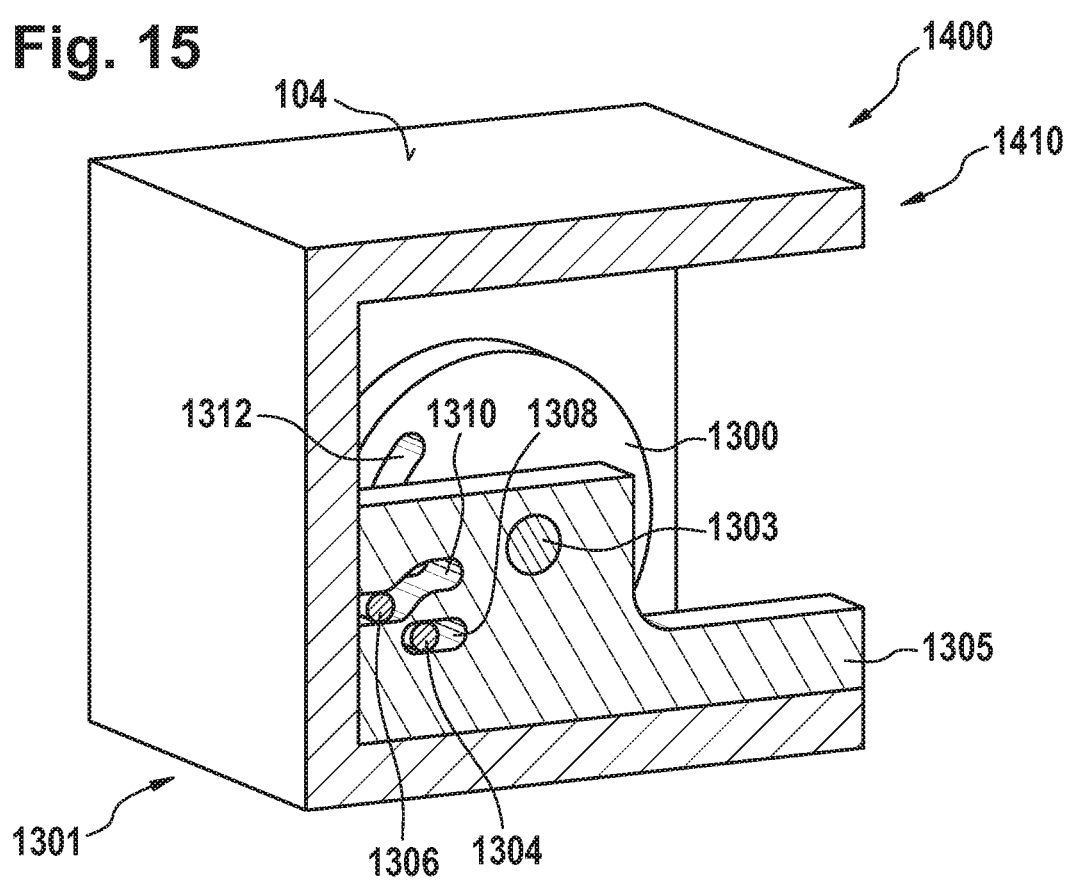
FIG. 15 shows a perspective view of the medical instrument of FIG. 13 at an alternative cross section.
Figure 16:
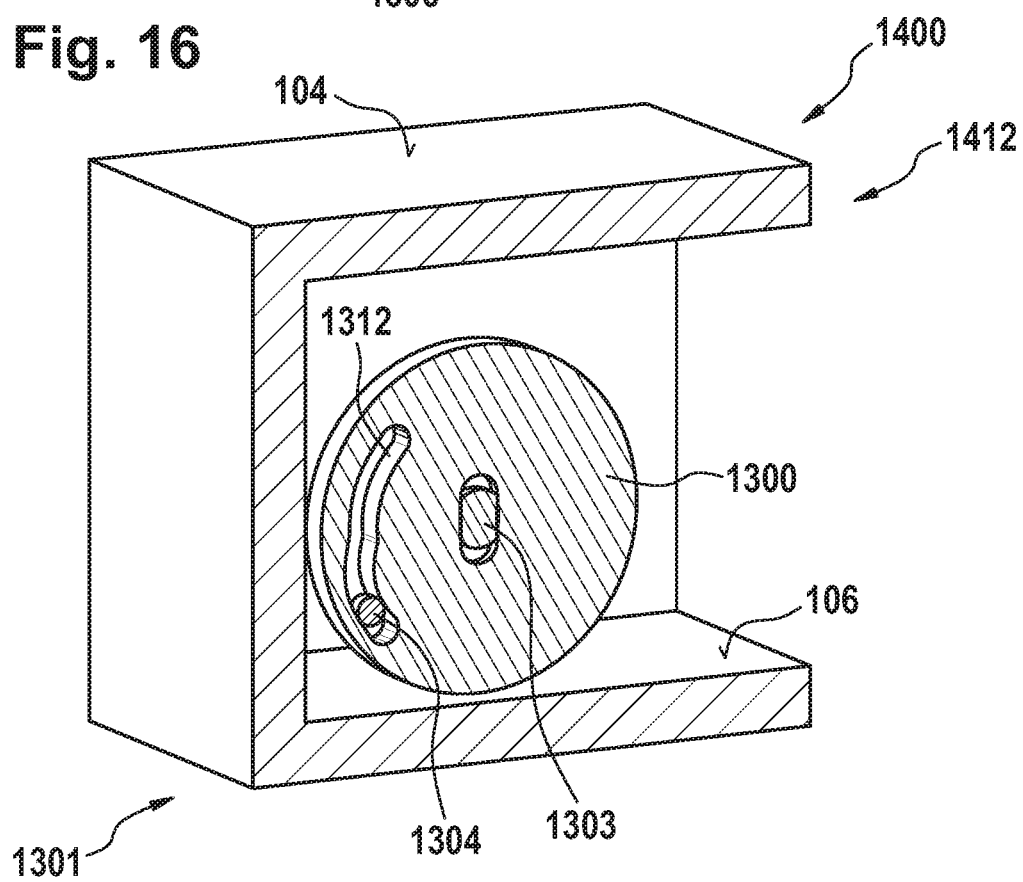
FIG. 16 shows a perspective view of the medical instrument of FIG. 13 at a further alternative cross section.
Figure 17:
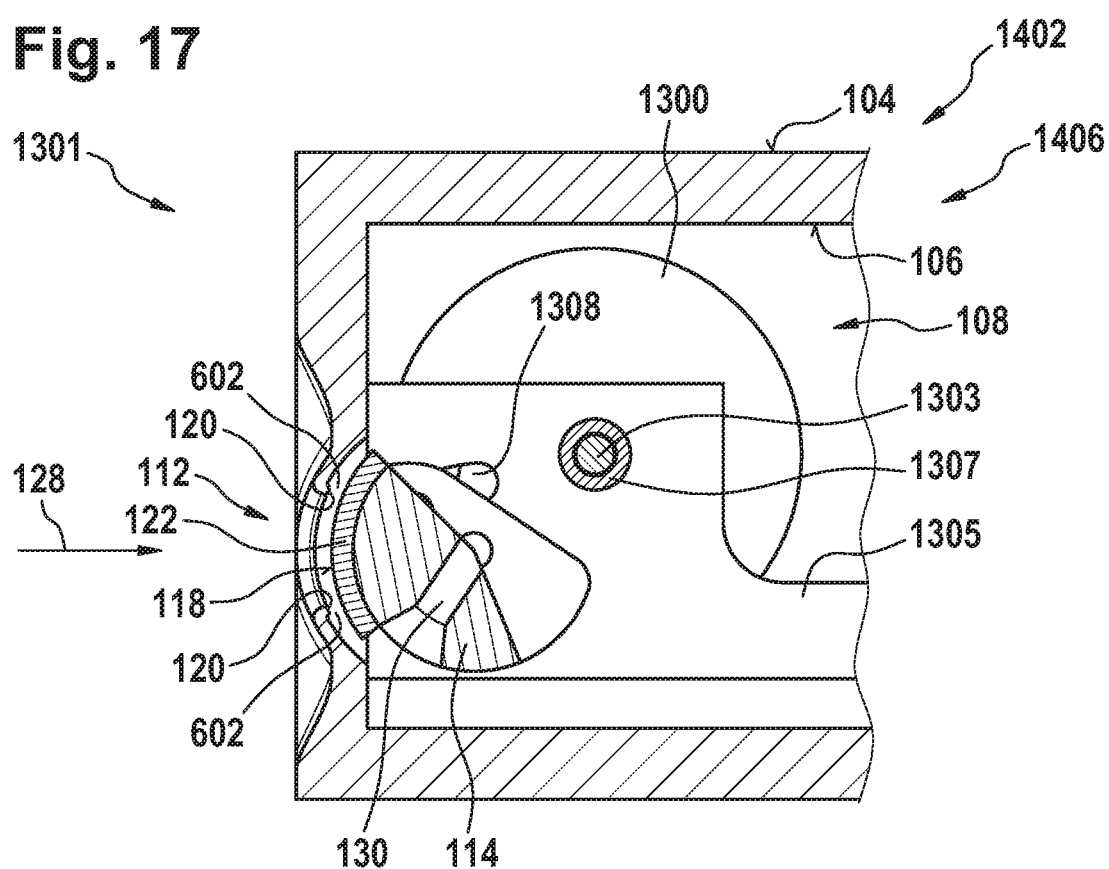
FIG. 17 shows the portion of the medical instrument of FIG. 13 as a cross sectional side view with the shutter in an intermediate position.
Figure 18:
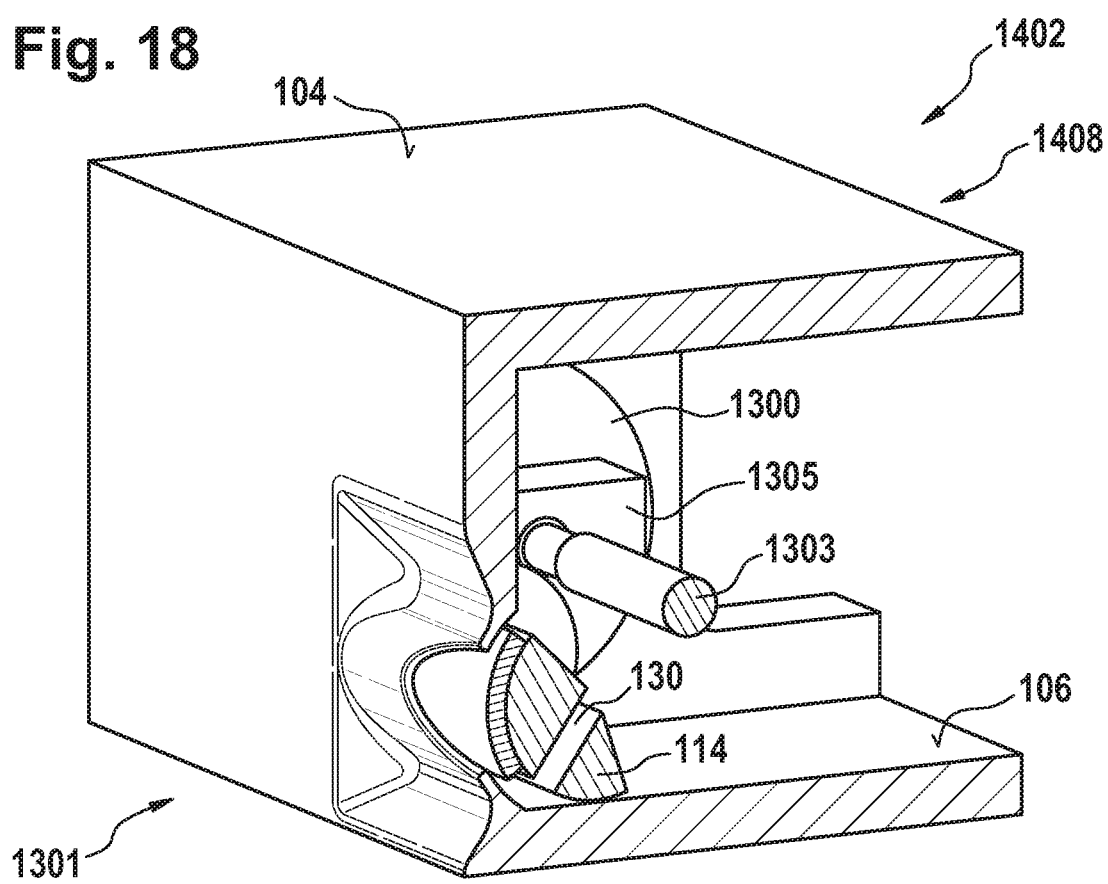
FIG. 18 shows a perspective view of the medical instrument of FIG. 17.

In FIGS. 13-16 the shutter is shown in a closed position 1400. In FIGS. 17-18 the shutter is shown in an intermediate position 1402. In FIGS. 21-24 the shutter is shown in an open position 1404.

Figure 13:
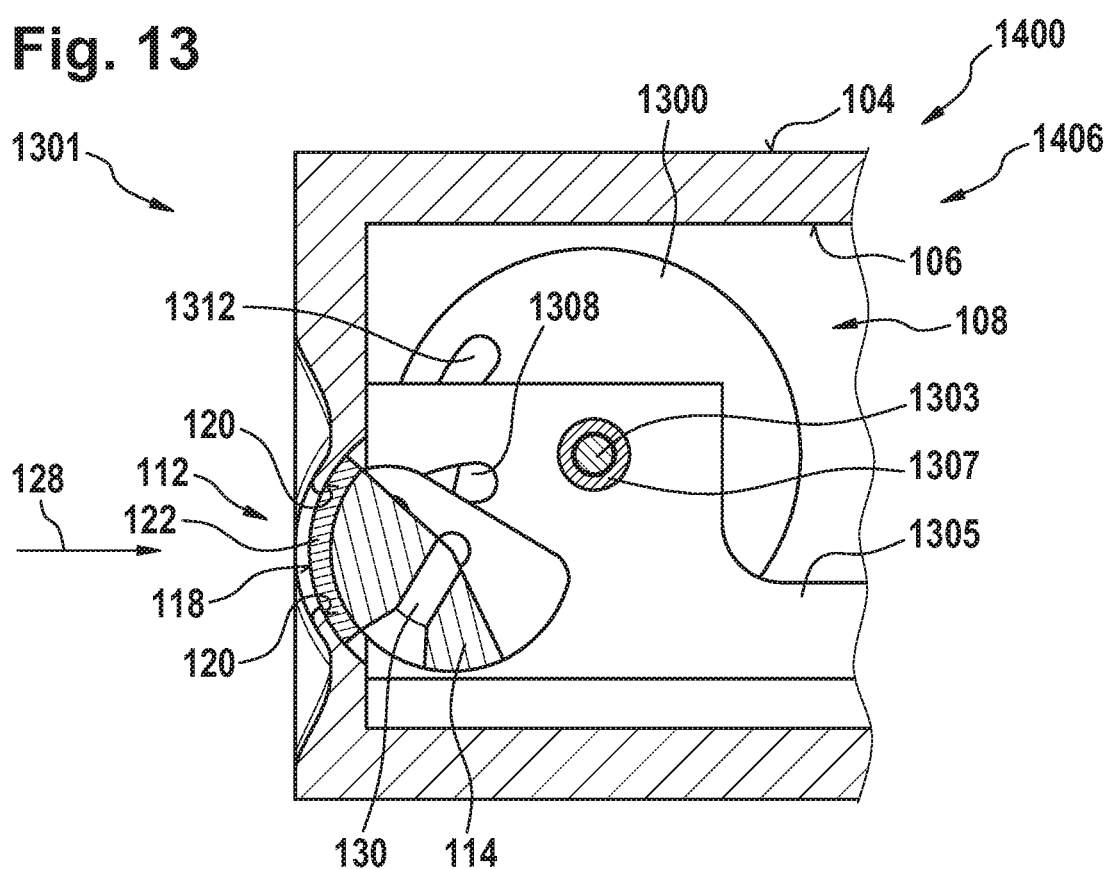
FIG. 13 shows a further example of a portion of a medical instrument in accordance with an embodiment of the present disclosure as a cross sectional side view with the shutter in a closed position.
Figure 14:
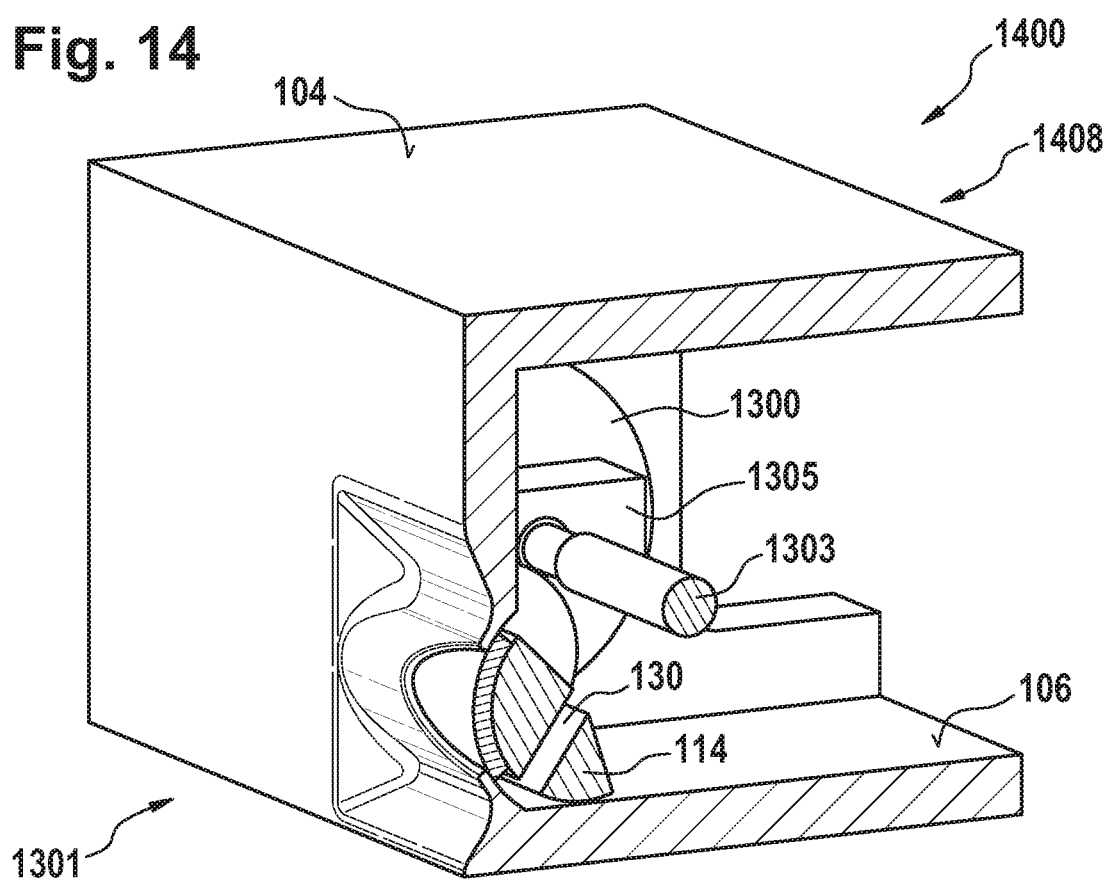
FIG. 14 shows a perspective view of the medical instrument of FIG. 13.
Figure 21:
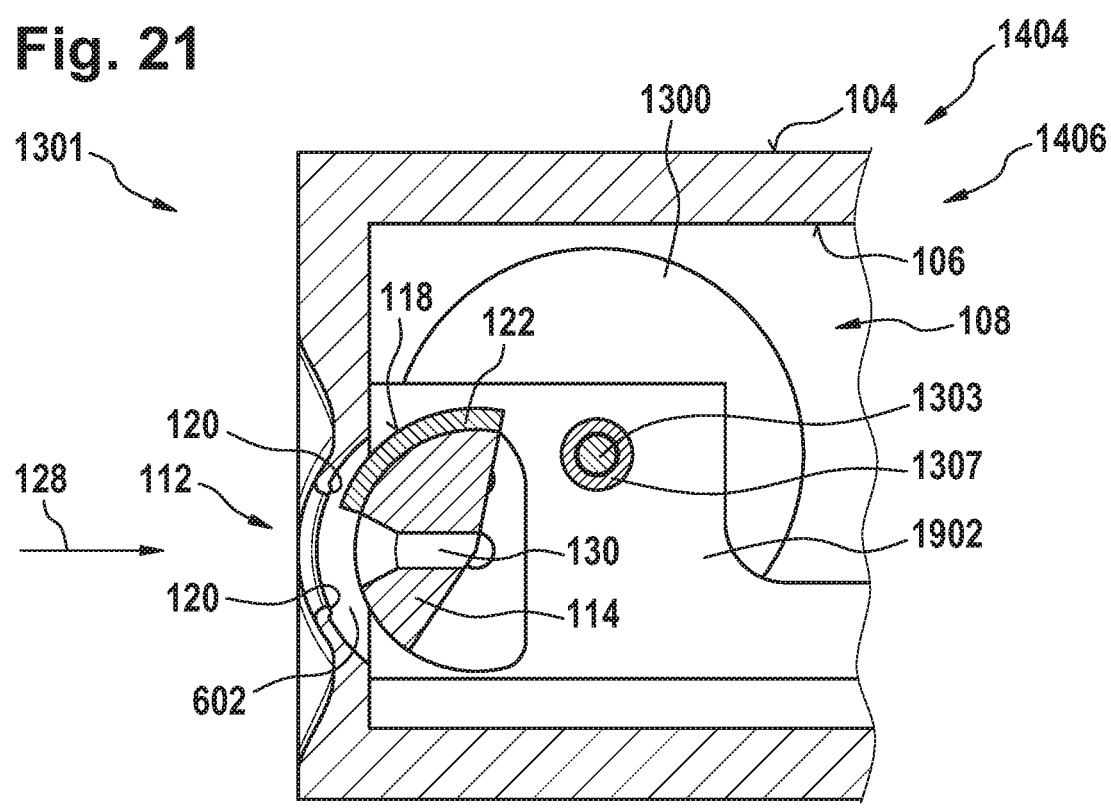
FIG. 21 shows the portion of the medical instrument of FIG. 13 as a cross sectional side view with the shutter in an open position.
Figure 22:
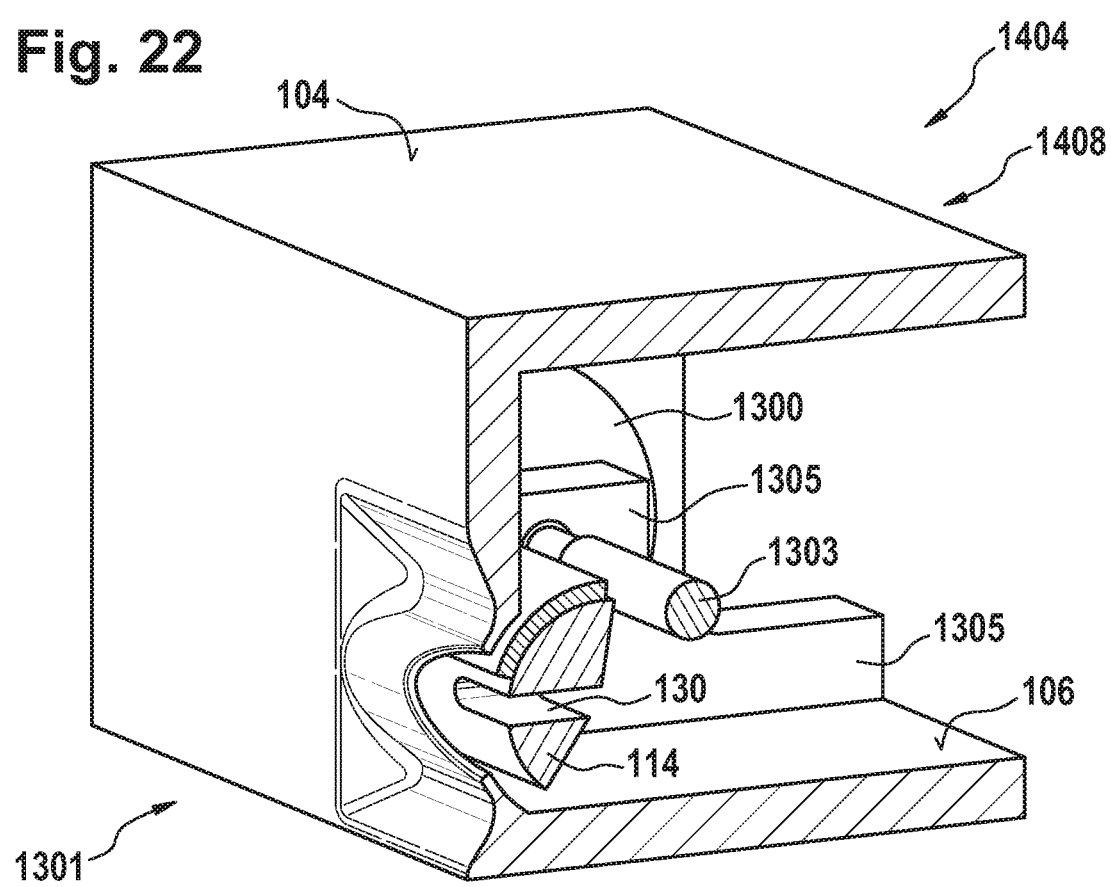
FIG. 22 shows a perspective view of the medical instrument of FIG. 21.
Figure 23:
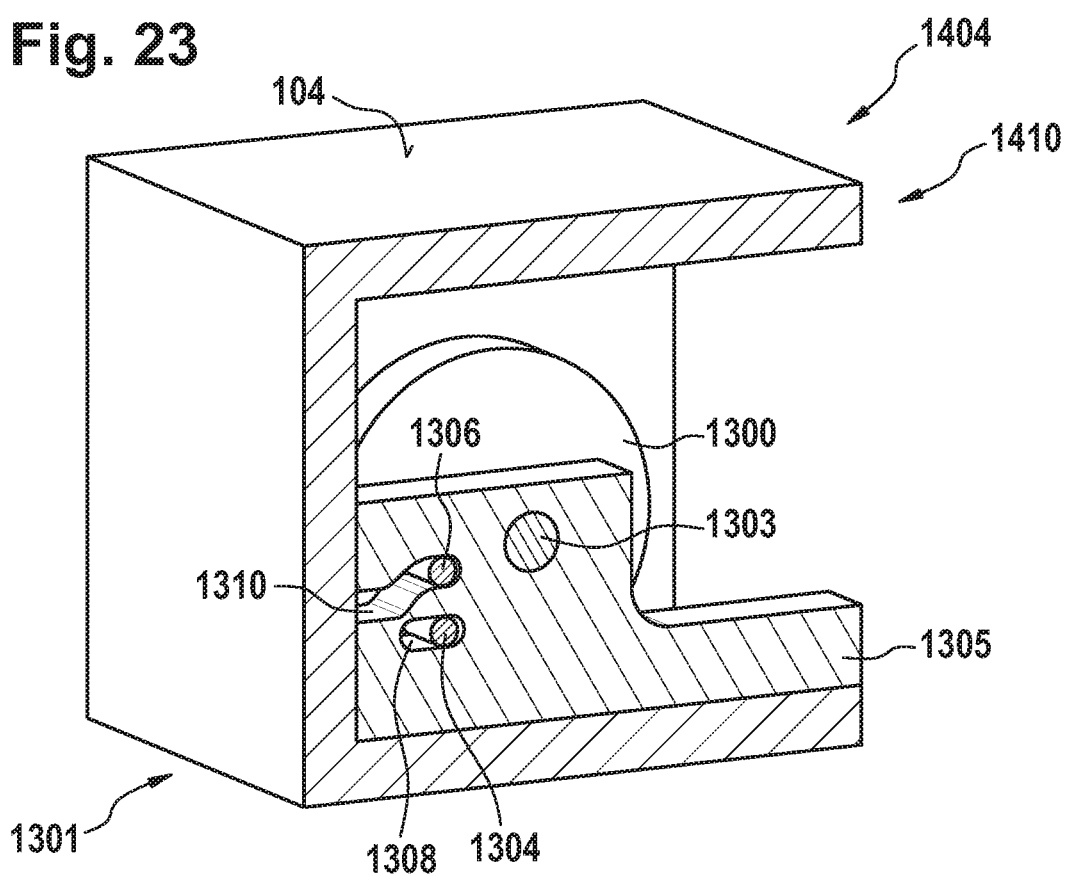
FIG. 23 shows a perspective view of the medical instrument of FIG. 21 at an alternative cross section.
Figure 24:
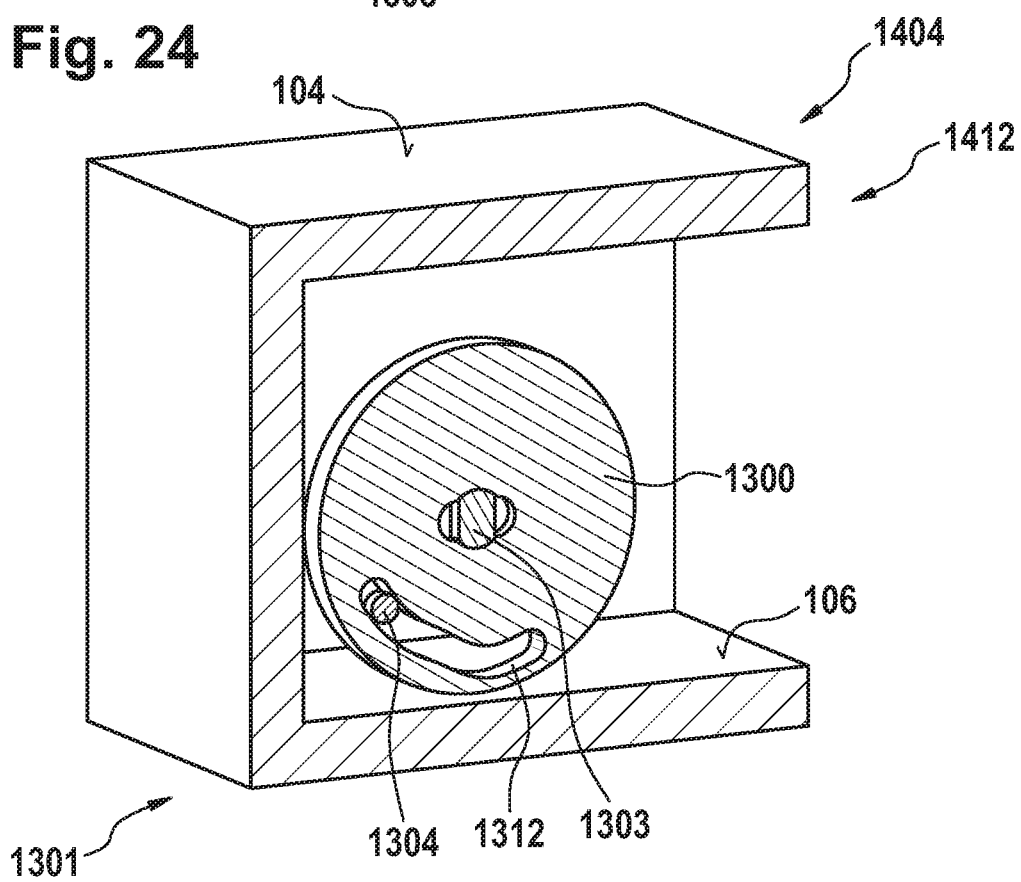
FIG. 24 shows a perspective view of the medical instrument of FIG. 21 at a further alternative cross section.

FIGS. 13, 17 and 21 show the shutter mechanism at a side view 1406, which is viewed from a first cross-section. FIGS. 14, 18 and 22 show a perspective view 1408 that is along the first cross-section that is also shown in FIGS. 13, 17 and 21. FIGS. 15, 19 and 23 show a further perspective view 1410 that is along a second cross-section. The second cross-section has been chosen to cut so that the shutter does not obstruct the view of the mechanism. FIGS. 16, 20 and 24 show a further perspective view 1412 along a third cross-section of the mechanism. The mechanism or a portion of the medical instrument 1301 shown in FIGS. 13-24 is similar to the mechanism shown in FIGS. 1-12. However, in FIGS. 13-24 there is a cam disc 1300 that is connected to a fixed support 1305 via a shaft 1303. A bearing 1307 connects the shaft 1303 to the fixed support 1305. The fixed support 1305 is connected to the inside 106 of the portion of the medical instrument 1301. The fixed support 1305 has a first pathway 1308 and a second pathway 1310. The cam disc 1300 has a third pathway 1312.

Attached to the shutter 114 are two moveable pivots. A first moveable pivot 1304 and a second moveable pivot 1306. The first 1304 and second 1306 moveable pivots have a fixed relative position to the shutter 114. The fixed support 1305 has the first pathway 1308 to guide the first moveable pivot 1304. The fixed support 1305 further has a second pathway 1310 that guides the second moveable pivot 1306.

The third pathway 1312 in the cam disc 1300 is also used to guide the first moveable pivot 1304. As the cam disc 1300 is rotated it drives the first moveable pivot. As the first and second moveable pivots have a fixed relationship with respect to the shutter 114 which causes the second moveable pivot 1306 to be driven along the second pathway 1310 and the first moveable pivot 1304 can be driven along the first pathway 1308. The mechanism illustrated in FIGS. 13-24 show a system where the shutter 114 is in the closed position and then pulls back before rotating into the open position. This may be particularly advantageous because it reduces the wear and tear on the first sealing surface 118. In FIG. 13 the shutter 114 is shown in the closed position. In FIG. 17 the shutter 114 is shown as having pulled away such that the first sealing surface 118 is no longer in contact with the second sealing surface 120. Finally, in FIG. 21 the shutter 114 rotates such that the test strip support 130 is in a position where it can now accept a test strip.

FIGS. 14, 18 and 22 show the same details as FIGS. 13, 17 and 21 except in perspective view. FIGS. 15, 19 and 23 show a cross-section partially through the fixed support 1305.

As the shutter 114 is opened FIGS. 15, 19 and 23 show the relative positions of the first moveable pivot 1304 in the first pathway 1308 and the second moveable pivot 1306 in the second pathway 1310. FIGS. 16, 20 and 24 show a cross-sectional view partially cut through the cam disc 1300. This illustrates the rotational location of the cam disc 1300 and also the position of the first moveable pivot 1304 within the third pathway 1312. The various cross-sectional views shown in these Figs. enable an understanding of how the mechanism of the portion of the medical instrument 1301 functions.

Figure 25:
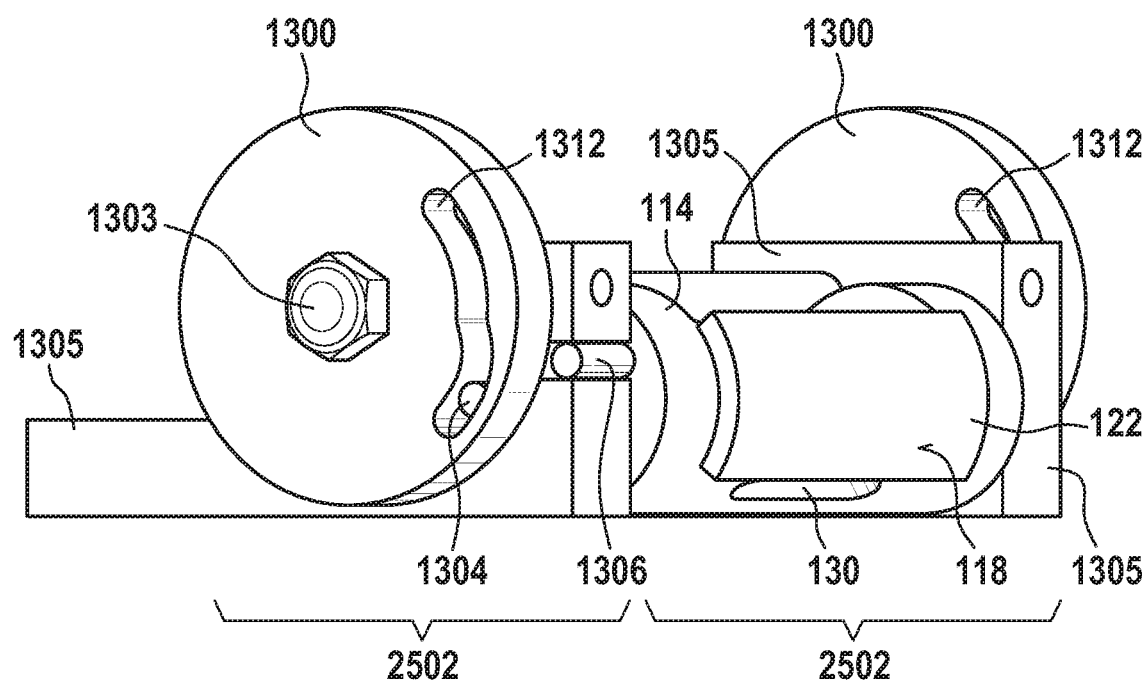
FIG. 25 illustrates the shutter and mechanism portions for the example illustrated in FIGS. 13 through 24.

FIG. 25 shows a further view of the shutter mechanism for the mechanism of FIGS. 13-24. In this example the shutter 114 is suspended by two mechanism portions 2502 that are mere images of each other. The shutter 114 is then supported on both sides by these mechanism portions 2502.

Figure 26:
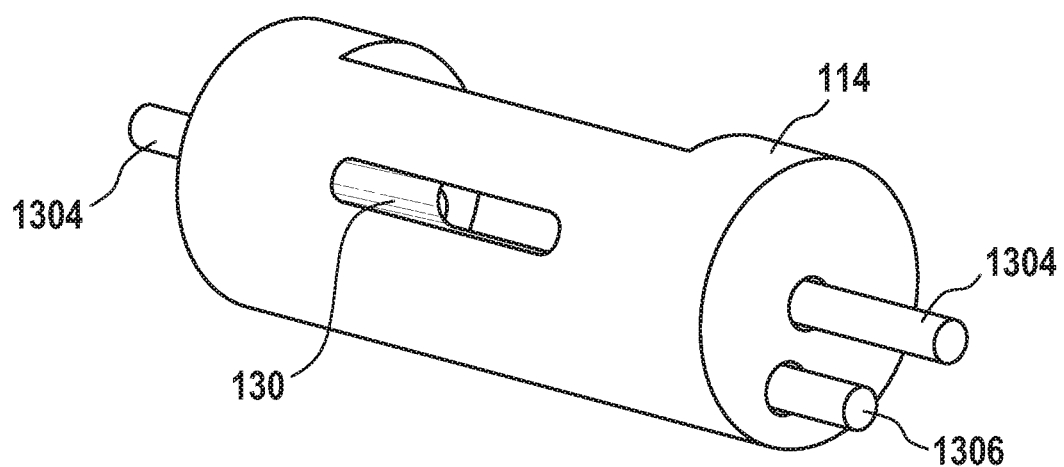
FIG. 26 illustrates the shutter, the first movable pivot and the second movable pivot for the example illustrated in FIGS. 13 through 25.

FIG. 26 shows the shutter 114 of the mechanism illustrated in FIGS. 13-25. It can be seen that the first moveable pivot 1304 and the second moveable pivot 1306 are fixed with respect to their location on the shutter 114.

Figure 27:
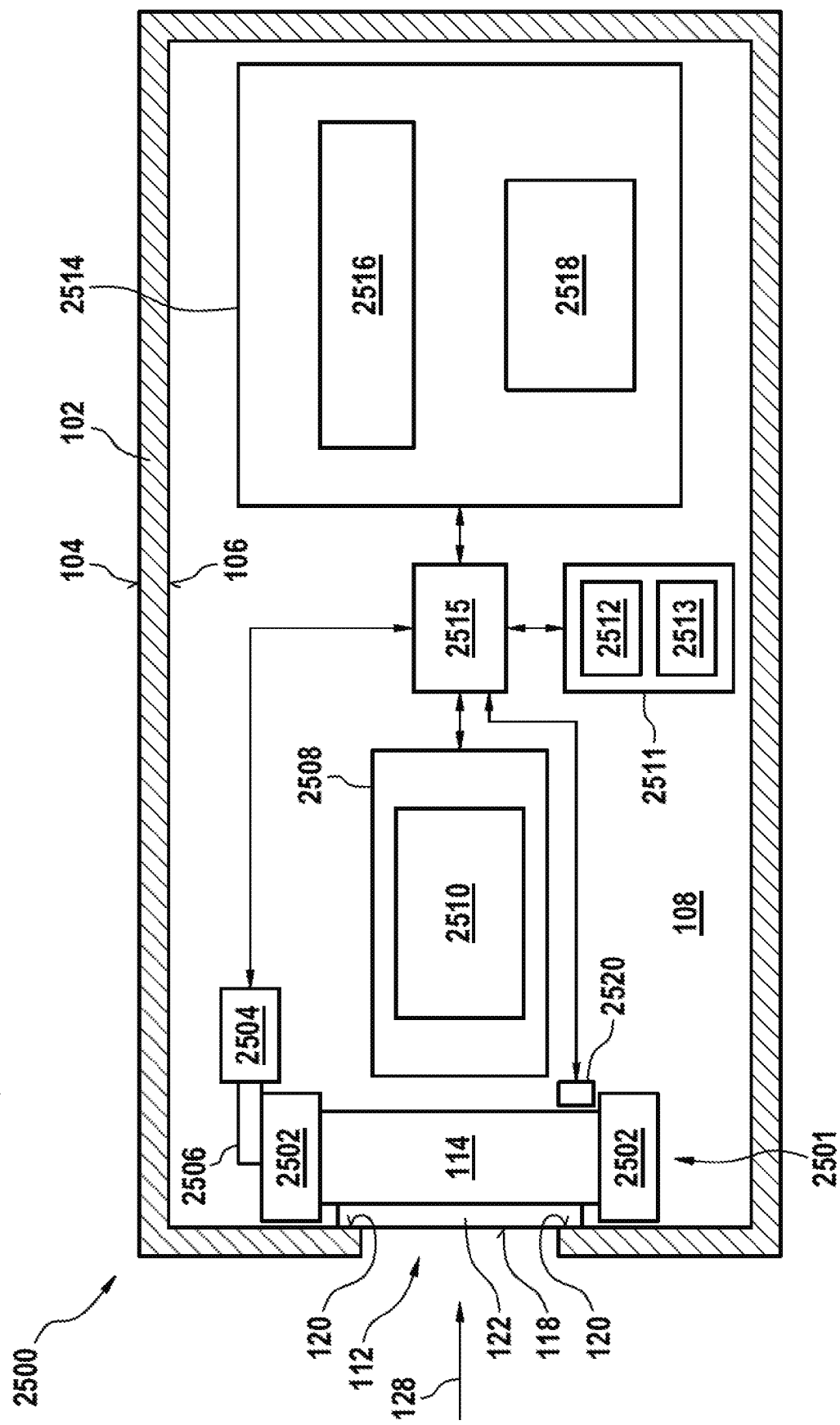
FIG. 27 illustrates an example of a medical instrument in accordance with an embodiment of the present disclosure.

FIG. 27 shows an example of a medical instrument 2500. The medical instrument has a housing 102 which has an exterior surface 104 and an internal surface 106. The internal surface 106 surrounds an interior volume 108. There is a test strip port 112 that is shown as being sealed by a shutter mechanism 2501. The shutter mechanism 2501 could be according to any one of the mechanisms shown in FIGS. 1-24. In this Fig. the shutter 114 is shown as being supported by two mechanism portions 2502. In other variants there is only one mechanism portion 2502. In this example equivalent mechanisms support the shutter 114 on both sides. Shown is a motor 2504 which has an actuator 2506 which is used to drive the mechanism 2501. The motor 2504 can be used to automatically open or close the shutter 114. In this Fig. the shutter is shown as being closed and the test strip port 112 is sealed. When the test strip port 112 is open a strip can be inserted into an analytical unit 2508. Inside the analytical unit 2508 there is a test strip mount 2510 which is configured for receive the test strip to perform a measurement.

Adjacent to the analytical unit 2508 and the shutter mechanism 2501 is a strip detector 2520. The strip detector 2520 is a mechanical or optical sensor which is used to detect the presence of a test strip within the medical instrument 2500. The medical instrument 2500 is further shown as containing a processor 2515. The processor 2515 is connected to the motor 2504, the analytical unit 2508, the optional strip detector 2520 and also a touch screen display 2514. The processor 2515 is further connected to a memory 2511. The processor 2515 is configured so that it can send and receive instructions for these components and control the operation and function of the medical instrument 2500. The memory 2511 is shown as containing a set of instructions 2512. Execution of the instructions 2512 enables the processor 2515 to control and operate the medical instrument 2500. The memory 2511 is further shown as containing at least one measurement 2513 that was acquired using the analytical unit 2508.

The touch screen 2514 is configured for displaying data and information as well as receiving input from an operator or user of the medical instrument 2500. For example, when the medical instrument 2500 has its test strip port sealed as is shown in FIG. 25; it may display a message 2516 which asks if the cleaning protocol has been finished. The message could for example be "Finished with cleaning protocols?" There is a graphical user interface control element 2518 or button which the operator can use to inform the processor 2515 that a cleaning protocol has been finished. The control element 2518 could example have the text "Yes" displayed on it. For example when the cleaning protocol is finished, the processor 2515 may control the motor 2504 such that the shutter 114 is opened and it is then possible to insert a test strip into the analytical unit and mount it properly within the test strip mount 2510 so that a further measurement 2513 can be performed.

Figure 28:
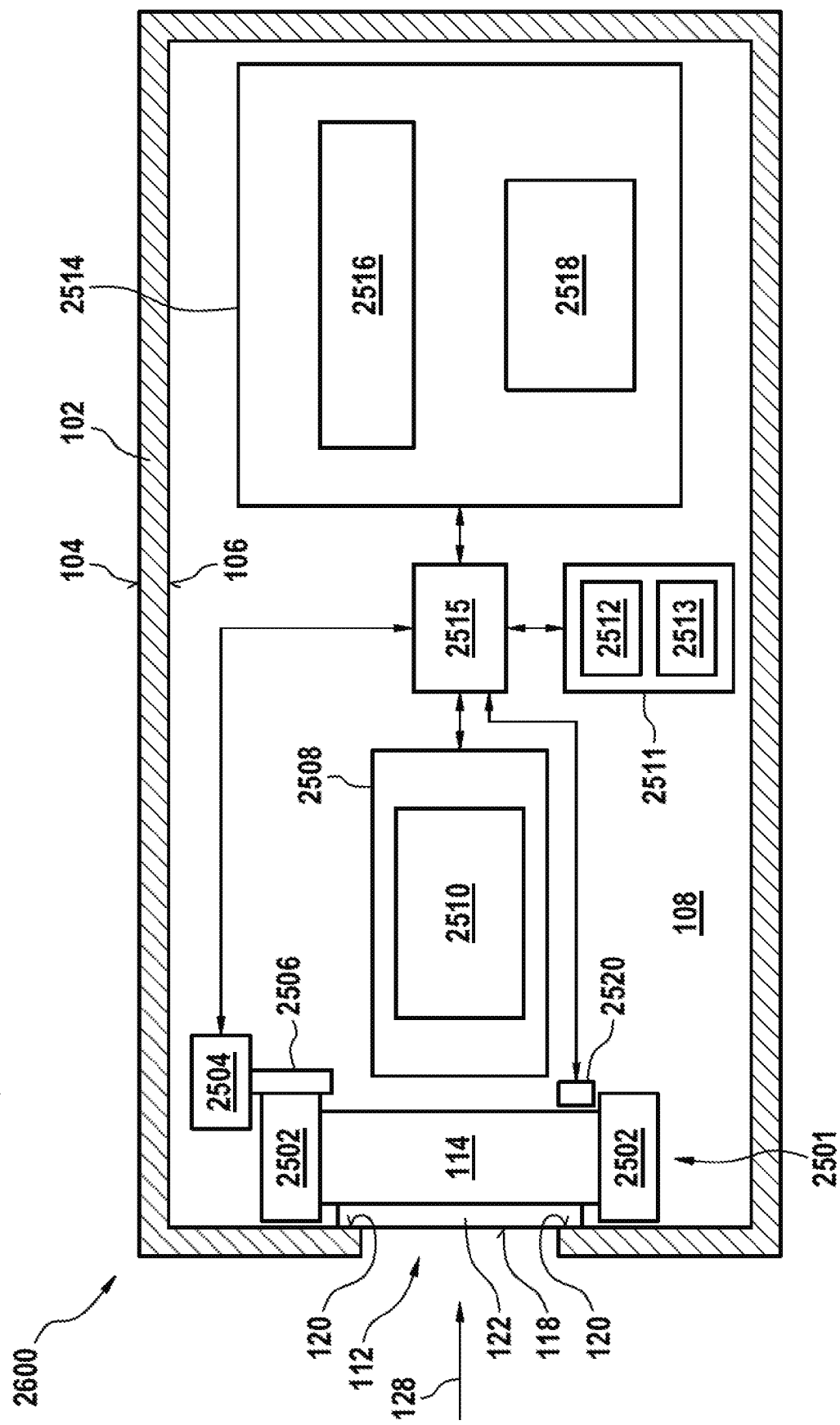
FIG. 28 illustrates an example of a medical instrument.

FIG. 28 shows a further example of a medical instrument 2600. The medical instrument 2600 is similar to the medical instrument 2500 shown in FIG. 25 except the motor 2504 and the actuator 2506 are shown as being configured differently that it is in FIG. 25.

Figure 29:
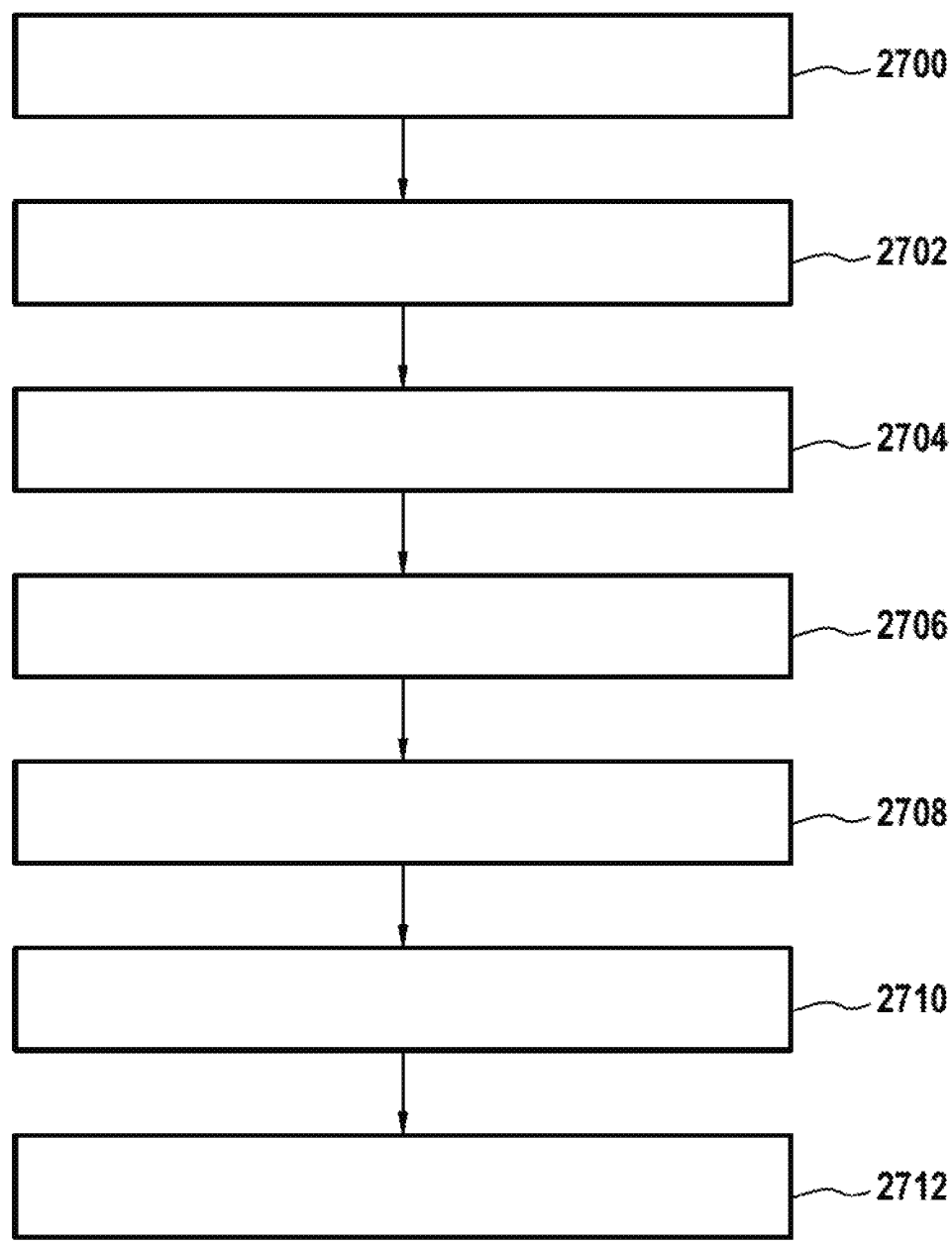
FIG. 29 shows a flow chart that illustrates a method of operating the medical instrument of FIG. 25 or 26.

FIG. 29 shows a flowchart which shows one method of operating the medical instrument 2500 of FIG. 25 or the medical instrument 2600 of FIG. 26. First in step 2700 the actuator motor 2504 is controlled to move the shutter 114 into the open position. In FIGS. 25 and 26 the actuator 2506 is shown as being moved by a motor 2504. In other examples the actuator for instance may be controlled or moved manually. Next in step 2702 a biological sample is placed onto a test strip.

Next in step 2704 a test strip is inserted into the test strip port 112 such that the test strip passes through the test strip support and into the test strip mount 2510. Next in step 2706 the test strip is analyzed with the analytical unit 2508 to perform the measurement 2513. Next in step 2708 the test strip is removed from the medical instrument 2500, 2600. Next in step 2710 the actuator 2506 is controlled to actuate the mechanism 2501 to move the shutter 114 into the closed position.

Finally in step 2712 the exterior surface 104 of the medical instrument 2500, 2600 is cleaned. The protocol for cleaning and disinfection the medical instrument 2500, 2600 may be performed with chemicals which easily damage the electronics and other components of the medical instrument 2500, 2600. For example in a clinical setting the medical instrument 2500, 2600 will likely be cleaned after every use or at least between use between different patients. The cleaning protocol may involve several steps. For example the protocol may begin with the medical instrument being wiped down to remove any obvious fluids or contaminants on the surface. Then, one or more steps where the medical instrument 2500, 2600 may be cleaned and/or disinfected with one or more chemical solutions may follow. Finally, the medical instrument 2500, 2600 may be dried. Once the cleaning and disinfection protocol has been finished then the operator or user may elect to open the mechanism 2501 in preparation for inserting another test strip.

Figure 30:
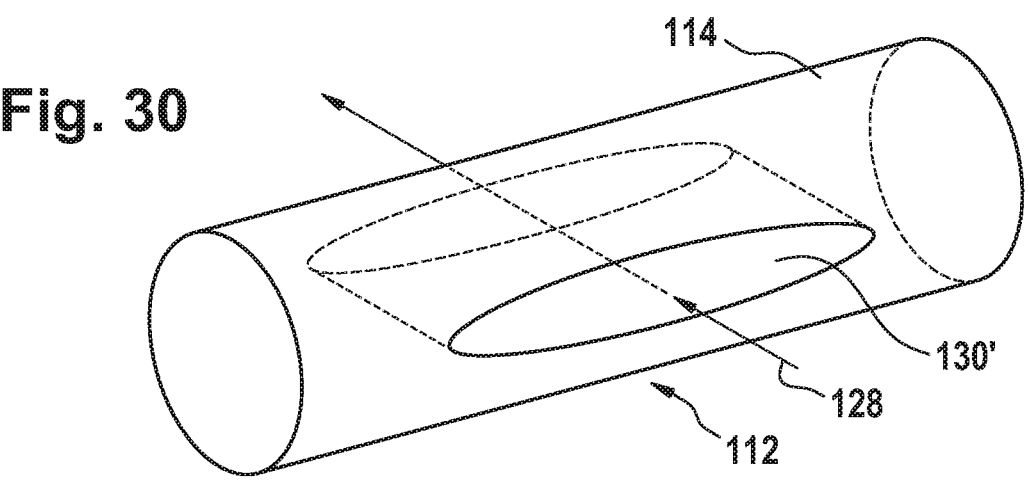
FIG. 30 illustrates an example of a test strip support in accordance with an embodiment of the present disclosure.

FIG. 30 shows an abstraction of a shutter 114 with a test strip support 130'. In this example the test strip support 130' has oval profile perpendicular to the insertion direction 128.

Figure 31:
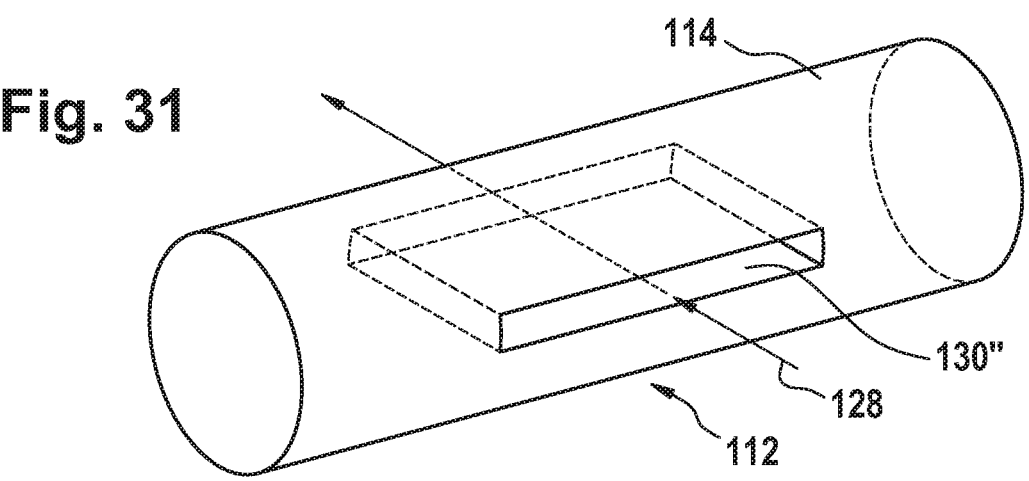
FIG. 31 illustrates a further example of a test strip support in accordance with an embodiment of the present disclosure.

FIG. 31 shows a further example of a shutter with a test strip support 130". In this example the test strip support 130" that has a rectangular profile perpendicular to the insertion direction 128.

Figure 32:
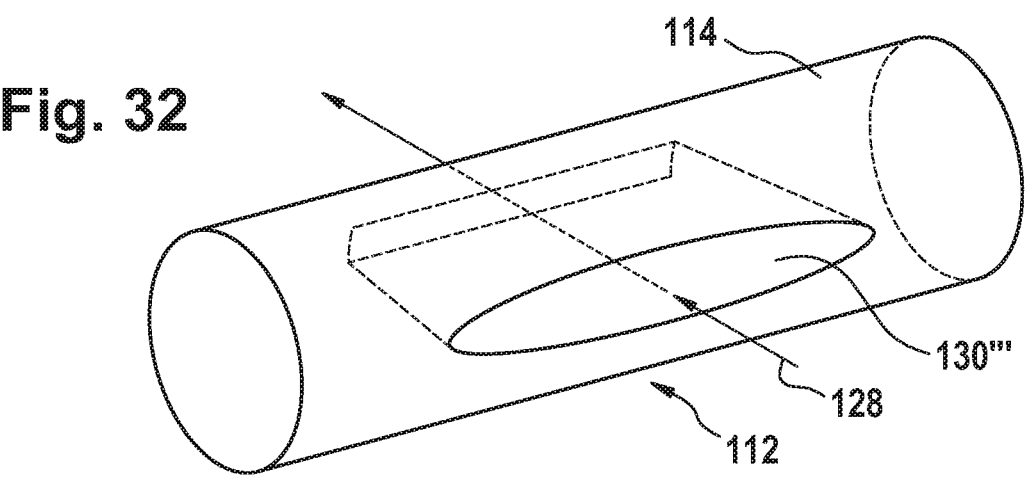
FIG. 32 illustrates a further example of a test strip support in accordance with an embodiment of the present disclosure.

FIG. 32 shows a further example of a shutter 114 with a test strip support 130'''. In this example the test strip support 130''' has a profile that transitions from oval perpendicular to the insertion direction 128 near the test strip support to a rectangular profile near the test strip mount when in the open position. The shutters in FIGS. 30-32 are all shown in the open position. The insertion direction 128 is aligned with the test strip supports 130', 130", 130'''.

LIST OF REFERENCE NUMERALS

- 100 portion of medical instrument
- 102 housing
- 104 exterior surface
- 106 internal surface
- 108 interior volume
- 110 test strip
- 112 test strip port
- 114 shutter
- 116 support structure
- 118 first sealing surface
- 120 second sealing surface
- 122 gasket material
- 124 pivot
- 126 direction of rotation
- 128 insertion direction
- 130 test strip support
- 130' test strip support
- 130" test strip support
- 130''' test strip support
- 300 first cylindrical axis
- 600 portion of medical instrument
- 602 gap
- 604 rotational axis or second cylindrical axis
- 1300 cam disk
- 1301 portion of medical instrument
- 1303 shaft
- 1304 first movable pivot
- 1305 fixed support
- 1306 second movable pivot
- 1307 bearing
- 1308 first pathway
- 1310 second pathway
- 1312 third pathway
- 1400 closed position
- 1402 intermediate position
- 1404 open position
- 1406 side view along first cross section
- 1408 perspective view along first cross section
- 1410 perspective view along second cross section
- 1412 perspective view along third cross section
- 2500 medical instrument
- 2501 shutter mechanism
- 2502 mechanism portion
- 2504 motor
- 2506 actuator
- 2508 analytical unit
- 2510 test strip mount
- 2511 memory
- 2512 instructions
- 2513 measurement
- 2514 touch screen
- 2515 processor
- 2516 message "finished with cleaning protocols?"
- 2518 graphical user interface control element
- 2520 strip detector
- 2600 medical instrument
- 2700 control the actuator to actuate the mechanism to move the shutter in the open position
- 2702 place the biological sample on the test strip
- 2704 insert a test strip into the test strip port such that the test strip passes through the test strip support and into the test strip mount
- 2706 analyze the test strip with the analytical unit to perform the measurement
- 2708 remove the test strip from the medical instrument
- 2710 control the actuator to actuate the mechanism to move the shutter in the closed position; and
- 2712 clean the exterior surface of the medical instrument.

It is noted that terms like "preferably," "commonly" and typically are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

For purposes of describing and defining the subject matter of the present disclosure it is noted that the terms "substantially" and "about" may be utilized herein to represent the inherent degree of uncertainly that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus, it is intended that the specification cover the modifications and variations of the various embodiments described herein, provided such modifications and variations come within the scope of the appended claims and their equivalents.

What is claimed is:

1. A method of operating a medical instrument, wherein the medical instrument is an analyzer for performing a measurement on a biological sample using a test strip, wherein the medical instrument comprises:

a housing with an exterior surface, wherein the housing comprises an internal surface surrounding an interior volume;

an analytical unit for analyzing the test strip, wherein the analytical unit is within the interior volume, wherein the analytical unit comprises a test strip mount configured for receiving the test strip to perform the measurement;

a test strip port between the exterior surface and the interior surface, wherein the test strip port is configured for receiving the test strip, wherein the test strip port is aligned with the test strip mount along an insertion direction;

a shutter for sealing the test strip port, wherein the shutter is configured for being in a open position and a closed position, wherein the shutter is within the interior volume, wherein the shutter is configured for sealing the test strip port when in the closed position, wherein the shutter comprises a test strip support, wherein the test strip support is aligned with the test strip port and the test strip mount when the shutter is in the open position, wherein the shutter has a first sealing surface, wherein the test strip port has a second sealing surface, wherein the first sealing surface and the second sealing surface are configured to mate in the closed position, wherein the shutter comprises a mechanism for moving the shutter between the open position and the closed position, wherein moving the shutter between the closed position and the open position comprises a rotation of the shutter perpendicular to the insertion direction; and an actuator for actuating the mechanism to move the shutter between the open position and the closed position;

wherein the method comprises the steps of:

controlling the actuator to actuate the mechanism to move the shutter in the open position;

placing the biological sample on the test strip;

inserting the test strip into the test strip port such that the test strip passes through the test strip support and into the test strip mount;

analyzing the test strip with the analytical unit to perform the measurement;

removing the test strip from the medical instrument;

controlling the actuator to actuate the mechanism to move the shutter in the closed position; and cleaning the exterior surface of the medical instrument.

2. A medical instrument, wherein the medical instrument is an analyzer for performing a measurement on a biological sample using a test strip, wherein the medical instrument comprises:

a housing with an exterior surface, wherein the housing comprises an internal surface surrounding a interior volume;

an analytical unit for analyzing the test strip, wherein the analytical unit is within the interior volume, wherein the analytical unit comprises a test strip mount configured for receiving the test strip to perform the measurement;

a test strip port between the exterior surface and the interior surface, wherein the test strip port is configured for receiving the test strip, wherein the test strip port is aligned with the test strip mount along an insertion direction;

a shutter for sealing the test strip port, wherein the shutter is configured for being in an open position and a closed position, wherein the shutter is within the interior volume, wherein the shutter is configured for sealing the test strip port when in the closed position, wherein the shutter comprises a test strip support, wherein the test strip support is aligned with the test strip port and the test strip mount when the shutter is in the open position, wherein the shutter has a first sealing surface, wherein the test strip port has a second sealing surface, wherein the first sealing surface and the second sealing surface are configured to mate in the closed position, wherein the shutter comprises a mechanism for moving the shutter between the open position and the closed position, wherein moving the shutter between the closed position and the open position comprises a rotation of the shutter perpendicular to the insertion direction; and an actuator for actuating the mechanism to move the shutter between the open position and the closed position; wherein the actuator comprises a motor, wherein the medical instrument further comprises a memory for storing machine executable instructions, wherein the medical instrument further comprises a processor for controlling the medical instrument, wherein execution of the machine executable instructions causes the processor to:

control the motor to actuate the mechanism to move the shutter in the open position;

analyze the test strip with the analytical unit to perform the measurement when the test strip is inserted into the test strip mount and the biological sample is placed on the test strip; and control the motor to actuate the mechanism to move the shutter in the closed position when the test strip is removed from the test strip mount and the test strip port.

3. The medical instrument of claim 2, wherein the medical instrument further comprises a user interface for receiving user input that indicates that the medical instrument has been cleaned, wherein execution of the machine executable instructions further cause the processor to control the motor to actuate the mechanism to move the shutter in the open position after receiving the user input.

4. The medical instrument of claim 2, wherein the medical instrument further comprises a detector for detecting if a test strip is inserted through the test strip port, wherein execution of the machine executable instructions further cause the processor to control the motor to place the shutter in the closed position after the detector indicates that the test strip is no longer inserted through the test strip port.

5. The medical instrument of claim 2, wherein the first sealing surface is cylindrical about a first cylindrical axis and wherein the second sealing surface is cylindrical about a second cylindrical axis, wherein the first cylindrical axis is parallel with the second cylindrical axis.

6. The medical instrument of claim 5, wherein the first sealing surface has a first convex cross section that is a circular arc with a first radius, wherein the second sealing surface has a second concave cross section that is a second circular arc with a second radius.

7. The medical instrument of claim 5, wherein the mechanism is a pivot that rotates the shutter about the first cylindrical axis, wherein the first cylindrical axis is coaxial with the second cylindrical axis.

8. The medical instrument of claim 5, wherein the mechanism is a pivot that rotates the shutter about a rotational axis, wherein the rotational axis is parallel to the first cylindrical axis, wherein the rotational axis is offset from the first cylindrical axis, and wherein any one of the following: the first radius is the same as the second radius and the first radius is smaller than the second radius.

9. The medical instrument of claim 2, wherein the mechanism is formed by the shutter, a cam disk, and a fixed support, wherein the cam disk is configured for rotating relative to the fixed support, wherein the fixed support is rigidly connected to the internal surface of the housing, wherein the shutter comprises a first movable pivot and a second movable pivot, wherein the fixed support comprises a first pathway for guiding the first movable pivot, wherein the fixed support comprises a second pathway for guiding the second movable pivot, and wherein the first cam disk comprises a third pathway for guiding the first movable pivot.

10. The medical instrument of claim 2, wherein the mechanism comprises two equivalent mechanism portions that support the shutter.

11. The medical instrument of claim 2, wherein the test strip support is a hole within the shutter.

12. The medical instrument of claim 11, wherein the test strip support has any one of the following: a rectangular profile perpendicular to the insertion direction when in the open position, an oval profile perpendicular to the insertion direction when in the open position, and a profile that transitions from oval profile near the test strip port to rectangular profile near the test strip mount when in the open position.

13. The medical instrument of claim 2, wherein the analytical unit is any one of the following: an optical test strip analyzer, an electrochemical test strip analyzer, and combinations thereof.

14. The medical instrument of claim 2, wherein the interior volume is hermetically sealed from the exterior surface when the shutter is in the closed position.

15. The medical instrument of claim 2, wherein the interior volume is watertight when the shutter is in the closed position.

16. The medical instrument of claim 2, wherein when the shutter is in the closed position the shutter and test strip port fit together so tightly that liquid is unable to enter the interior volume through the test strip port.

* * * * *